US009144663B2

(12) United States Patent
Ahlberg et al.

(10) Patent No.: US 9,144,663 B2
(45) Date of Patent: Sep. 29, 2015

(54) METHODS AND DEVICES FOR REPAIRING AND/OR PREVENTING PARAVALVULAR LEAKAGE POST-IMPLANTATION OF A VALVE PROSTHESIS

(71) Applicant: Medtronic, Inc., Minneapolis, MN (US)

(72) Inventors: Sarah Ahlberg, Mounds View, MN (US); Cynthia Clague, Mounds View, MN (US); Susan Peterson, Santa Rosa, CA (US); Scott Mosher, Santa Rosa, CA (US); Karan Punga, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 436 days.

(21) Appl. No.: 13/659,668

(22) Filed: Oct. 24, 2012

(65) Prior Publication Data
US 2014/0114402 A1 Apr. 24, 2014

(51) Int. Cl.
*A61F 2/24* (2006.01)
*A61M 25/00* (2006.01)
*A61B 17/12* (2006.01)
*A61M 31/00* (2006.01)
*A61M 25/10* (2013.01)

(52) U.S. Cl.
CPC ........ *A61M 25/0082* (2013.01); *A61B 17/1219* (2013.01); *A61B 17/12036* (2013.01); *A61B 17/12122* (2013.01); *A61B 17/12136* (2013.01); *A61B 17/12186* (2013.01); *A61F 2/2418* (2013.01); *A61F 2/2457* (2013.01); *A61B 2017/12054* (2013.01); *A61F 2/2409* (2013.01); *A61F 2210/0085* (2013.01); *A61F 2220/005* (2013.01); *A61F 2230/005* (2013.01); *A61F 2230/008* (2013.01); *A61F 2230/0013* (2013.01); *A61F 2230/0067* (2013.01); *A61F 2230/0078* (2013.01); *A61F 2250/0069* (2013.01); *A61M 31/005* (2013.01); *A61M 2025/0087* (2013.01); *A61M 2025/1052* (2013.01)

(58) Field of Classification Search
CPC .................................. A61F 2/243; A61F 2/24
USPC ................................................. 623/2.11–2.19
See application file for complete search history.

(56) References Cited

U.S. PATENT DOCUMENTS

| 5,458,639 | A | 10/1995 | Tsukashima et al. |
|---|---|---|---|
| 6,500,147 | B2 | 12/2002 | Omaleki et al. |
| 6,554,795 | B2 | 4/2003 | Bagaoisan et al. |
| 6,676,692 | B2 | 1/2004 | Rabkin et al. |
| 6,736,827 | B1 | 5/2004 | McAndrew et al. |
| 7,258,696 | B2 | 8/2007 | Rabkin et al. |
| 7,276,078 | B2 | 10/2007 | Spenser et al. |
| 7,780,725 | B2 | 8/2010 | Haug et al. |
| 8,083,732 | B2 | 12/2011 | Arless et al. |
| 2003/0171773 | A1* | 9/2003 | Carrison ........................ 606/213 |

(Continued)

Primary Examiner — Suzette J Gherbi

(57) ABSTRACT

Devices and methods for delivering a sealing element post-implantation of valve prosthesis that functions to occlude or fill gaps present between the valve prosthesis and the native valve tissue, thereby reducing, minimizing, or eliminating leaks there through. In a first method, an injectable material is placed within a native valve sinus to form a sealing element that presses native valve leaflets against an outer surface of a heart valve prosthesis. In a second method, an injectable sealing material or a preformed annular sealing component is positioned between the outer surface or perimeter of a heart valve prosthesis and native heart valve tissue. In a third method, a preformed sealing element or component is placed within a heart valve prosthesis to press the prosthesis against native valve tissue.

20 Claims, 17 Drawing Sheets

(56) References Cited

U.S. PATENT DOCUMENTS

| | | |
|---|---|---|
| 2003/0199963 A1 | 10/2003 | Tower et al. |
| 2003/0199971 A1 | 10/2003 | Tower et al. |
| 2004/0111111 A1 | 6/2004 | Lin |
| 2007/0293944 A1* | 12/2007 | Spenser et al. ............... 623/2.11 |
| 2008/0243245 A1 | 10/2008 | Thambar |
| 2009/0099653 A1 | 4/2009 | Suri et al. |
| 2010/0168844 A1 | 7/2010 | Toomes et al. |
| 2010/0185274 A1* | 7/2010 | Moaddeb et al. ............ 623/1.24 |
| 2010/0280595 A1* | 11/2010 | Bilge et al. .................. 623/1.23 |
| 2011/0054466 A1 | 3/2011 | Rothstein et al. |
| 2011/0098802 A1 | 4/2011 | Braido et al. |
| 2011/0172765 A1 | 7/2011 | Nguyen et al. |
| 2011/0208297 A1* | 8/2011 | Tuval et al. .................. 623/2.17 |
| 2011/0264206 A1 | 10/2011 | Tabor |
| 2012/0035722 A1 | 2/2012 | Tuval |
| 2012/0052040 A1* | 3/2012 | Hunter et al. ................. 424/78.3 |
| 2012/0101572 A1 | 4/2012 | Kovalsky et al. |
| 2013/0317418 A1* | 11/2013 | Freyman et al. ................. 604/24 |
| 2014/0018910 A1* | 1/2014 | Moaddeb et al. ............ 623/2.11 |
| 2014/0214157 A1* | 7/2014 | Bortlein et al. .............. 623/2.11 |
| 2014/0271533 A1* | 9/2014 | Freyman et al. ........... 424/78.38 |
| 2015/0012085 A1* | 1/2015 | Salahieh et al. ............. 623/2.11 |

* cited by examiner

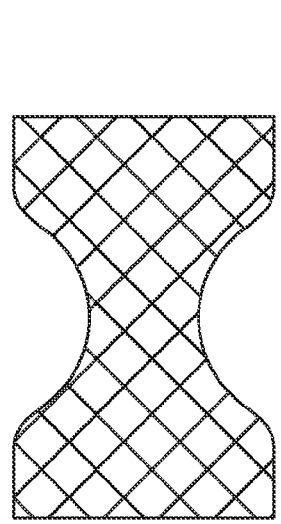
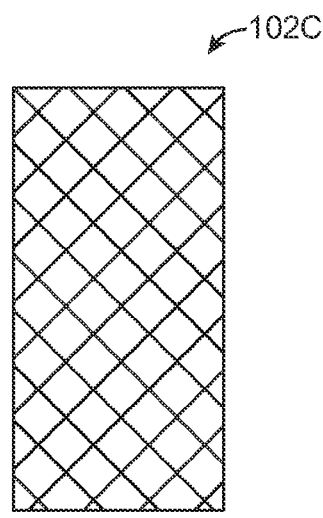
FIG. 1B
FIG. 1C
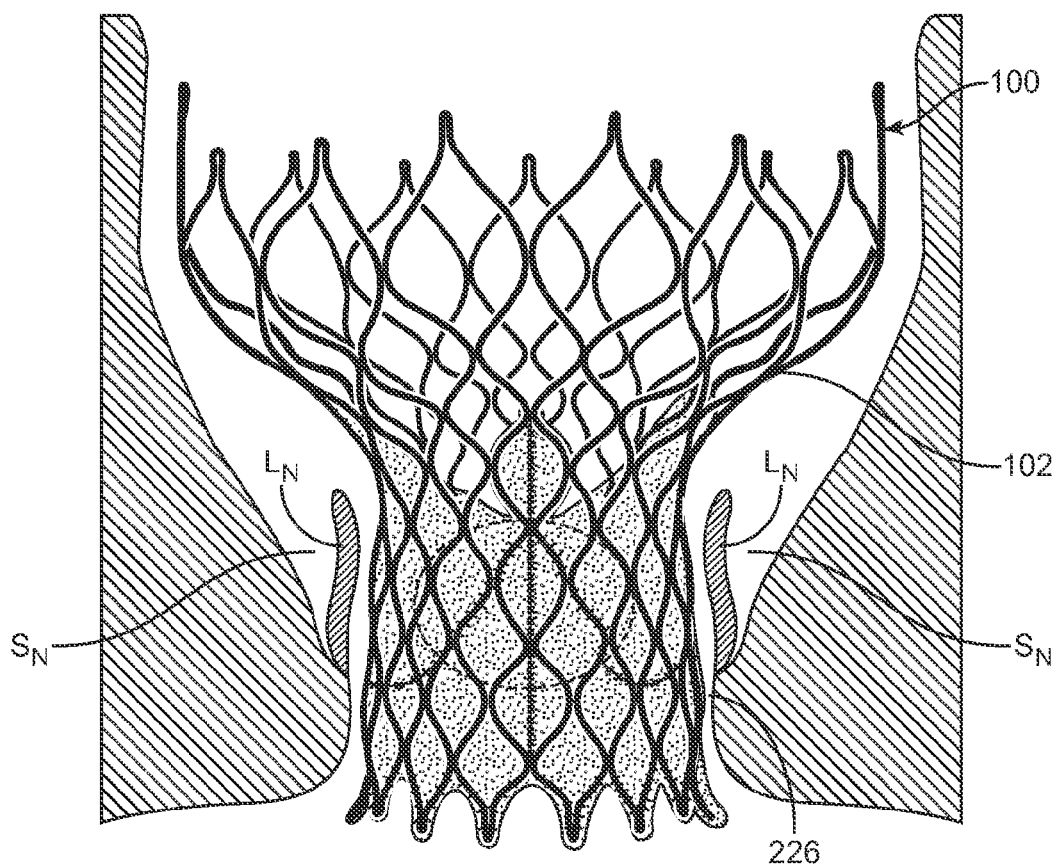
FIG. 2

METHODS AND DEVICES FOR REPAIRING AND/OR PREVENTING PARAVALVULAR LEAKAGE POST-IMPLANTATION OF A VALVE PROSTHESIS

FIELD OF THE INVENTION

The present invention relates to heart valve prostheses and methods of repairing and/or preventing paravalvular leakage. More specifically, the present invention relates to sealing material or elements that are applied post-implantation of a valve prosthesis to seal gaps between a valve frame and native valve tissue.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Patent Application Publication No. 2003/0199963 A1, both filed by Tower et al., each of which is incorporated by reference herein in its entirety.

Although transcatheter delivery methods have provided safer and less invasive methods for replacing a defective native heart valve, leakage between the implanted prosthetic valve and the surrounding native tissue is a recurring problem. Leakage sometimes occurs due to the fact that minimally invasive and percutaneous replacement of cardiac valves typically does not involve actual physical removal of the diseased or injured heart valve. Rather, the replacement stented prosthetic valve is delivered in a compressed condition to the valve site, where it is expanded to its operational state within the mitral valve. Calcified or diseased native leaflets are pressed to the side walls of the native valve by the radial force of the stent frame of the prosthetic valve. These calcified leaflets do not allow complete conformance of the stent frame with the native valve and can be a source of paravalvular leakage (PVL). Significant pressure gradients across the valve cause blood to leak through the gaps between the implanted prosthetic valve and the calcified anatomy.

Embodiments hereof are related to methods of repairing or preventing paravalvular leakage after implantation of the heart valve prosthesis.

BRIEF SUMMARY OF THE INVENTION

Embodiments hereof relate to a method of preventing and/or repairing paravalvular leakage. According to one embodiment hereof, a catheter is advanced to a previously implanted valve prosthesis. The catheter is configured to deliver an injectable sealing material. The sealing material is injected adjacent to the implanted valve prosthesis within a native valve sinus of the native valve via the catheter. The sealing material is allowed to expand and solidify in situ to form a sealing element that presses a native valve leaflet against the implanted valve prosthesis to close and/or prevent gaps between the implanted valve prosthesis and native valve tissue to repair and/or prevent paravalvular leakage.

According to another embodiment hereof, a catheter is advanced to a previously implanted valve prosthesis. The catheter is configured to deliver an injectable sealing material. The sealing material is injected around an outer surface of the implanted valve via the catheter. The sealing material is allowed to expand and solidify in situ to form an annular sealing element that extends between the outer surface of the implanted valve prosthesis and native valve tissue to close and/or prevent gaps between the implanted valve prosthesis and native valve tissue to repair and/or prevent paravalvular leakage.

According to another embodiment hereof, a catheter including a preformed annular sealing component mounted thereon is advanced to a previously implanted valve prosthesis. The preformed annular sealing component is positioned onto the implanted valve prosthesis, wherein the sealing component closes and/or prevents gaps between the implanted valve prosthesis and native valve tissue to prevent and/or repair paravalvular leakage.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1B is a side view illustration of an alternative configuration of a heart valve prosthesis for use in embodiments hereof.

FIG. 1C is a side view illustration of an alternative configuration of a heart valve prosthesis for use in embodiments hereof.

FIG. 2 is a side view illustration of the heart valve prosthesis of FIG. 1 implanted within a native valve annulus.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of heart valves, the invention may also be used where it is deemed useful in other valved intraluminal sites that are not in the heart. For example, the present invention may be applied to venous valves as well. Furthermore, there is no intention to be bound by any expressed or implied theory presented in the preceding technical field, background, brief summary or the following detailed description.

Figure 1:
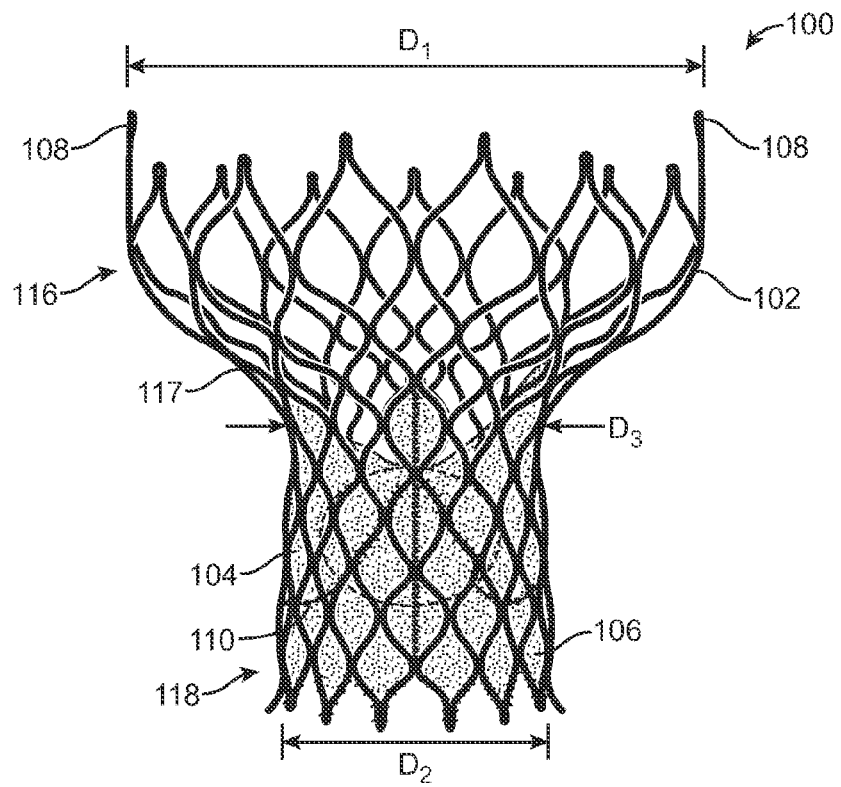
FIG. 1 is a side view illustration of an exemplary heart valve prosthesis for use in embodiments hereof.

FIG. 1 depicts an exemplary heart valve prosthesis 100. Heart valve prosthesis 100 is illustrated herein in order to facilitate description of the methods and devices to prevent and/or repair paravalvular leakage according to embodiments hereof. It is understood that any number of alternate heart valve prostheses can be used with the methods and devices described herein. Heart valve prosthesis 100 is merely exemplary and is described in more detail in U.S. Patent Application Pub. No. 2011/0172765 to Nguyen et al., which is herein incorporated by reference in its entirety.

Heart valve prosthesis 100 includes an expandable stent or frame 102 that supports a prosthetic valve component within the interior of stent 102. In embodiments hereof, stent 102 is self-expanding to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that stent 102 has a mechanical memory to return to the expanded or deployed configuration. Mechanical memory may be imparted to the wire or tubular structure that forms stent 102 by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety. In another embodiment hereof, stent 102 is balloon-expandable.

Figure 1A:
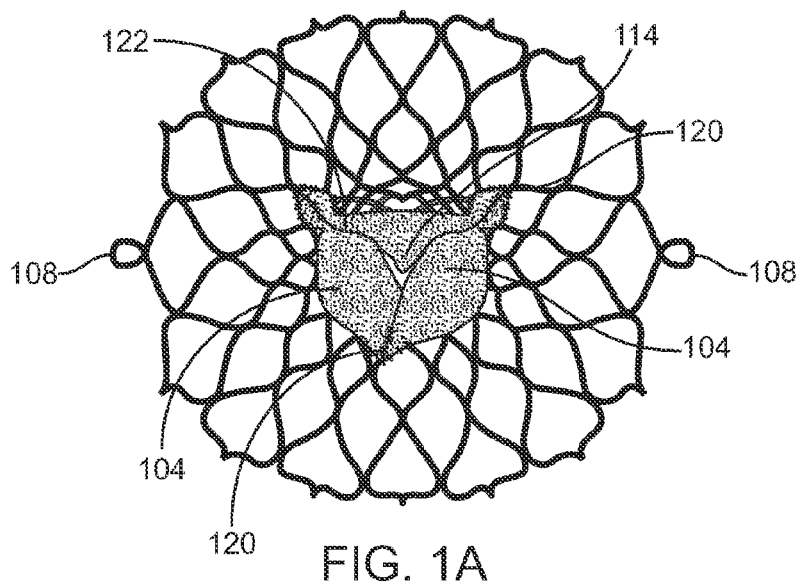
FIG. 1A is a top view illustration of the heart valve prosthesis of FIG. 1.

In the embodiment depicted in FIGS. 1 and 1A, stent 102 of valve prosthesis 100 has a deployed configuration including an enlarged first end or section 116, a constriction or waist region 117, and a second end or section 118. Enlarged first section 116 has nominal deployed diameter $D_1$, second section 118 has nominal deployed diameter $D_2$, and constriction region 117 has deployed substantially fixed diameter $D_3$. Each section of stent 102, may be designed with a number of different configurations and sizes to meet the different requirements of the location in which it may be implanted. When configured as a replacement for an aortic valve, second section 118 functions as an inflow end of heart valve prosthesis 100 and extends into and anchors within the aortic annulus of a patient's left ventricle, while first section 116 functions as an outflow end of heart valve prosthesis 100 and is positioned in the patient's ascending aorta. When configured as a replacement for a mitral valve, enlarged first section 116 functions as an inflow end of heart valve prosthesis 100 and is positioned in the patient's left atrium, while second section 118 functions as an outflow end of heart valve prosthesis 100 and extends into and anchors within the mitral annulus of a patient's left ventricle. For example, U.S. Patent Application Publication Nos. 2012/0101572 to Kovalsky et al. and 2012/0035722 to Tuval, each of which are herein incorporated by reference in their entirety, illustrate heart valve prostheses configured for placement in a mitral valve. Each section of stent 102 may have the same or different cross-section which may be for example circular, ellipsoidal, rectangular, hexagonal, rectangular, square, or other polygonal shape, although at present it is believed that circular or ellipsoidal may be preferable when the valve prosthesis is being provided for replacement of the aortic or mitral valve. As alternatives to the deployed configuration of FIGS. 1 and 1A, the stent/valve support frame may have an hourglass configuration 102B shown in FIG. 1B, a generally tubular configuration 102C as shown in FIG. 1C, or other stent configuration or shape known in the art for valve replacement. Stent 102 also may include eyelets 108 that extend from first end 116 thereof for use in loading the heart valve prosthesis 100 into a delivery catheter (not shown).

As previously mentioned, heart valve prosthesis 100 includes a prosthetic valve component within the interior of stent 102. The prosthetic valve component is capable of blocking flow in one direction to regulate flow there through via valve leaflets 104 that may form a bicuspid or tricuspid replacement valve. FIG. 1A is an end view of FIG. 1 and illustrates an exemplary tricuspid valve having three leaflets 104, although a bicuspid leaflet configuration having two leaflets or a monocuspid leaflet configuration having only one leaflet may alternatively be used in embodiments hereof. More particularly, if heart valve prosthesis 100 is configured for placement within a native valve having three leaflets such as the aortic, tricuspid, or pulmonary valves, heart valve prosthesis 100 includes three valve leaflets 104. If heart valve prosthesis 100 is configured for placement within a native valve having two leaflets such as the mitral valve, heart valve prosthesis 100 includes two valve leaflets 104. Valve leaflets 104 are sutured or otherwise securely and sealingly attached to the interior surface of stent 102 and/or graft material 106 which encloses or lines stent 102 as would be known to one of ordinary skill in the art of prosthetic tissue valve construction. Referring to FIG. 1, leaflets 104 are attached along their bases 110 to graft material 106, for example, using sutures or a suitable biocompatible adhesive. Adjoining pairs of leaflets are attached to one another at their lateral ends to form commissures 120, with free edges 122 of the leaflets forming coaptation edges that meet in area of coaptation 114.

Leaflets 104 may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 104 include DACRON® polyester commercially available from Invista North America S.A.R.L. of Wilmington, Del., other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Graft material 106 may also be a natural or biological material such as pericardium or another membranous tissue such as intestinal submucosa. Alternatively, graft material 106 may be a low-porosity woven fabric, such as polyester, Dacron fabric, or PTFE, which creates a one-way fluid passage when attached to the stent. In one embodiment, graft material 106 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

Delivery of heart valve prosthesis 100 may be accomplished via a percutaneous transfemoral approach or a transapical approach directly through the apex of the heart via a thoracotomy, or may be positioned within the desired area of the heart via different delivery methods known in the art for accessing heart valves. During delivery, the prosthetic valve remains compressed until it reaches a target diseased native heart valve, at which time the heart valve prosthesis 100 can be released from the delivery catheter and expanded in situ via self-expansion or alternatively balloon-expansion. The delivery catheter is then removed and heart valve prosthesis 100 remains deployed within the native target heart valve.

FIG. 2 is a side view illustration of heart valve prosthesis 100 implanted within a native heart valve, which is shown in section, having native leaflets $L_N$ and corresponding native sinuses $S_N$. When heart valve prosthesis 100 is deployed within the valve annulus of a native heart valve, stent 102 expands within native valve leaflets $L_N$ of the patient's defective valve, retaining the native valve leaflets in a permanently open state. The native valve annulus may include surface irregularities on the inner surface thereof, and as a result one or more gaps or cavities 226 may be present or may form between the perimeter of heart valve prosthesis 100 and the native valve annulus. For example, calcium deposits may be present on the native valve leaflets (e.g., stenotic valve leaflets) and/or shape differences may be present between the native heart valve annulus and prosthesis 100. For example, in some cases native annuli are not perfectly rounded and have indentations corresponding to the commissural points of the native valve leaflets. As a result, a prosthesis having an approximately circular shape does not provide an exact fit in a native valve. These surface irregularities, whatever their underlying cause, can make it difficult for conventional prosthetic valves to form a blood tight seal between the prosthetic valve and the inner surface of the valve annulus, causing undesirable paravalvular leakage and/or regurgitation at the implantation site.

Figure 3:
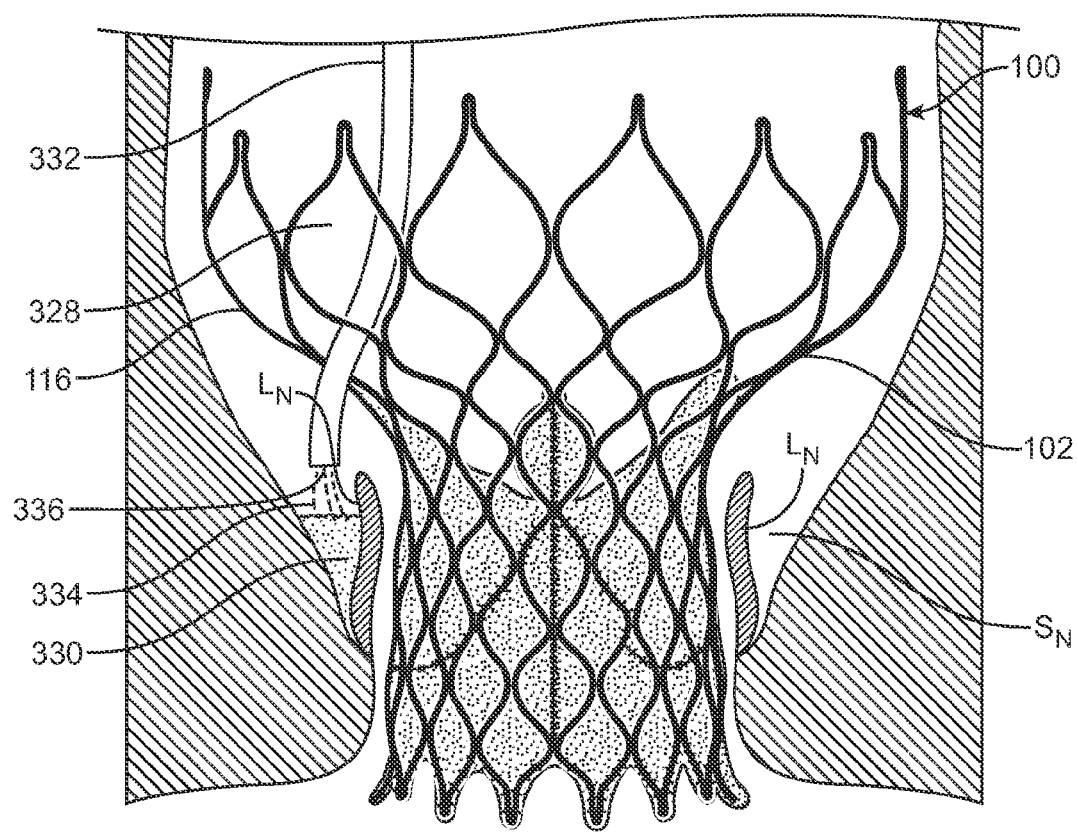
FIG. 3 is a side view illustration of a method of repairing or preventing paravalvular leakage according to an embodiment hereof, wherein sealing material is injected within a native valve sinus to press native valve tissue against a previously implanted heart valve prosthesis.
Figure 4:
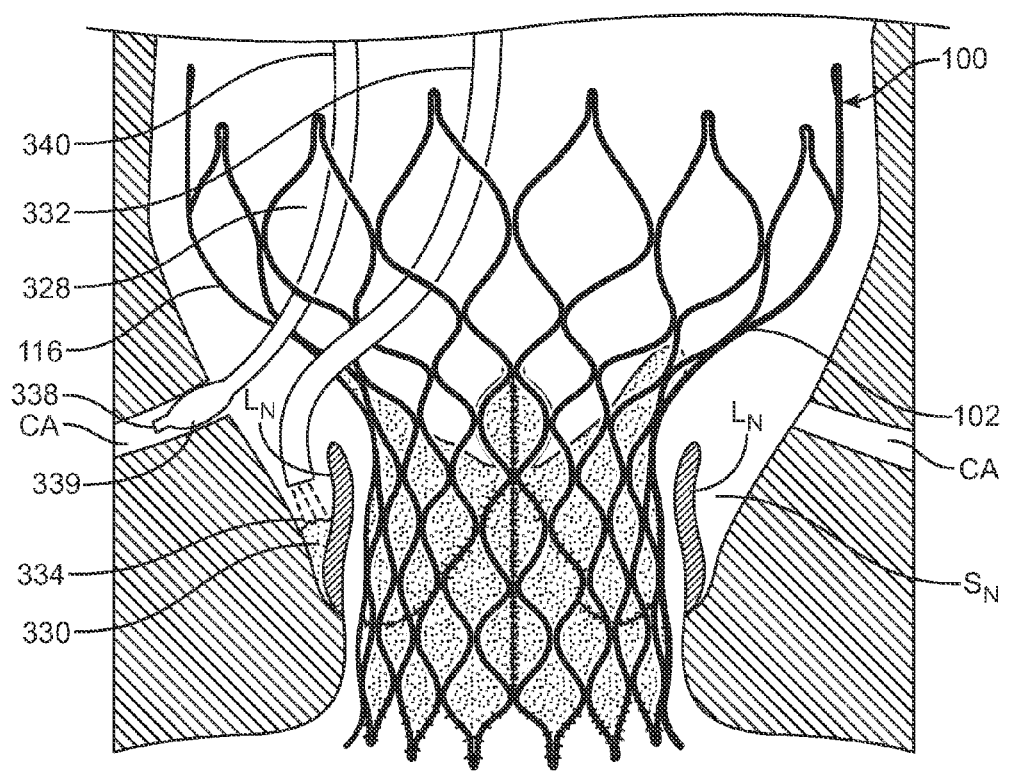
FIG. 4 is a side view illustration of a method of repairing or preventing paravalvular leakage according to an embodiment hereof, wherein a blocking catheter is placed within a coronary artery ostium for protection thereof when sealing material is injected within a native valve sinus to press native valve tissue against a previously implanted heart valve prosthesis.
Figure 5:
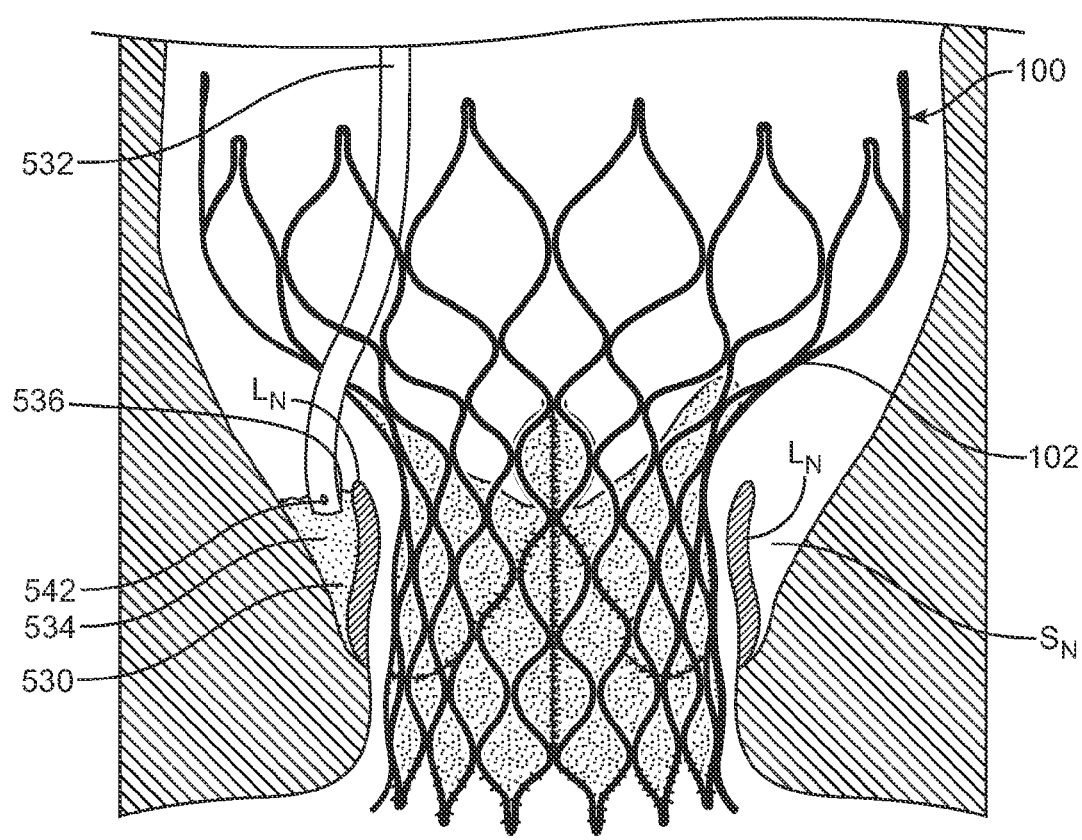
FIG. 5 is a side view illustration of a method of repairing or preventing paravalvular leakage according to an embodiment hereof, wherein sealing material is injected within a native valve sinus to press native valve tissue against a previously implanted heart valve prosthesis and heat is utilized to expand and/or solidify the sealing material in situ.

Embodiments hereof relate to methods for delivering a sealing element post-implantation of heart valve prosthesis 100 that functions to occlude or fill gaps 226, thereby reducing, minimizing, or eliminating leaks there through. "Sealing element" as used herein includes injectable material that forms a sealing element in situ or a preformed annular sealing component or element. FIGS. 3-5 relate to embodiments hereof in which injectable material is placed within a native valve sinus to form a sealing element that presses native valve leaflets against an outer surface of a heart valve prosthesis, FIGS. 6-10 and 14A-14D relate to embodiments hereof in which injectable sealing material or a preformed annular sealing component is positioned between the outer surface or perimeter of a heart valve prosthesis and a native heart valve annulus, and FIGS. 11-13 relates to embodiments hereof in which a preformed sealing element or component is placed within a heart valve prosthesis to press the prosthesis against native valve tissue.

In an embodiment hereof shown in FIG. 3, a sealing element 330 is positioned within a native valve sinus $S_N$ and functions to push native valve leaflet $L_N$ against the outside surface or perimeter of heart valve prosthesis 100, thereby filling any gaps which are present between heart valve prosthesis 100 and the native valve annulus and preventing paravalvular leakage. Sealing element 330 is formed after implantation of heart valve prosthesis 100 via percutaneous injection of an injectable, self-expanding substance such as gel or foam. More particularly, a delivery catheter 332 is advanced such that a distal end 336 thereof is located adjacent to a native valve sinus $S_N$. Because first end 116 of stent 102 employs relatively large cells or openings 328 that are not covered by graft material, prosthesis 100 does not obstruct subsequent catheter access to the native valve sinuses. Catheter 332 may be for example a catheter such as the ProFlo™ Angiographic Catheter or the Site Seer Catheter, both available from Medtronic, Inc. of Minneapolis, Minn., which adapted for use herein to deliver an injectable, self-expanding substance, or any diagnostic or therapeutic catheter suitable for delivery of an injectable substance such as a contrast medium or therapeutic substance. A self-expanding injectable substance 334 is delivered through a lumen (not shown) to distal end 336 of catheter 332, and is injected into a native valve sinus $S_N$. Suitable materials for self-expanding injectable substance 334 include but are not limited to hydrogel or a collagen foam/sponge similar to the material commercially available under the trademark Angioseal.

Once self-expanding injectable substance 334 exits catheter 332, it self-expands within native valve sinus $S_N$ and pushes native valve leaflet $L_N$ against the outside surface or perimeter of heart valve prosthesis 100, thereby substantially filling any gaps which are present between heart valve prosthesis 100 and native valve tissue. "Substantially" as utilized herein means that blood flow through the target gap or cavity is occluded or blocked, or stated another way blood is not permitted to flow there through. After delivery from catheter 332, self-expanding injectable substance 334 solidifies or firms upon contact with or exposure to a liquid, i.e., blood, such that it forms sealing element 330 that remains in situ within native valve sinus $S_N$ to provide a seal between an outer surface of prosthesis 100 and the inner surface of native valve leaflet $L_N$. Sealing element 330 pushes or displaces one or more of the native valve leaflets $L_N$ against prosthesis 100 to provide a seal between an outer surface of the prosthesis 100 and the displaced native valve leaflets $L_N$. The seal blocks retrograde blood flow around the outside of prosthesis 100, thereby minimizing and/or eliminating any paravalvular leakage at the implantation site. The shape and size of sealing element 330 depending on shape and size of the native valve sinuses $S_N$. As is generally known in the art, the size and dimensions of areas of a native valve will vary widely from one patient to another, thus the size and dimensions of the sealing element or component 330 may vary accordingly.

Figure 3A:
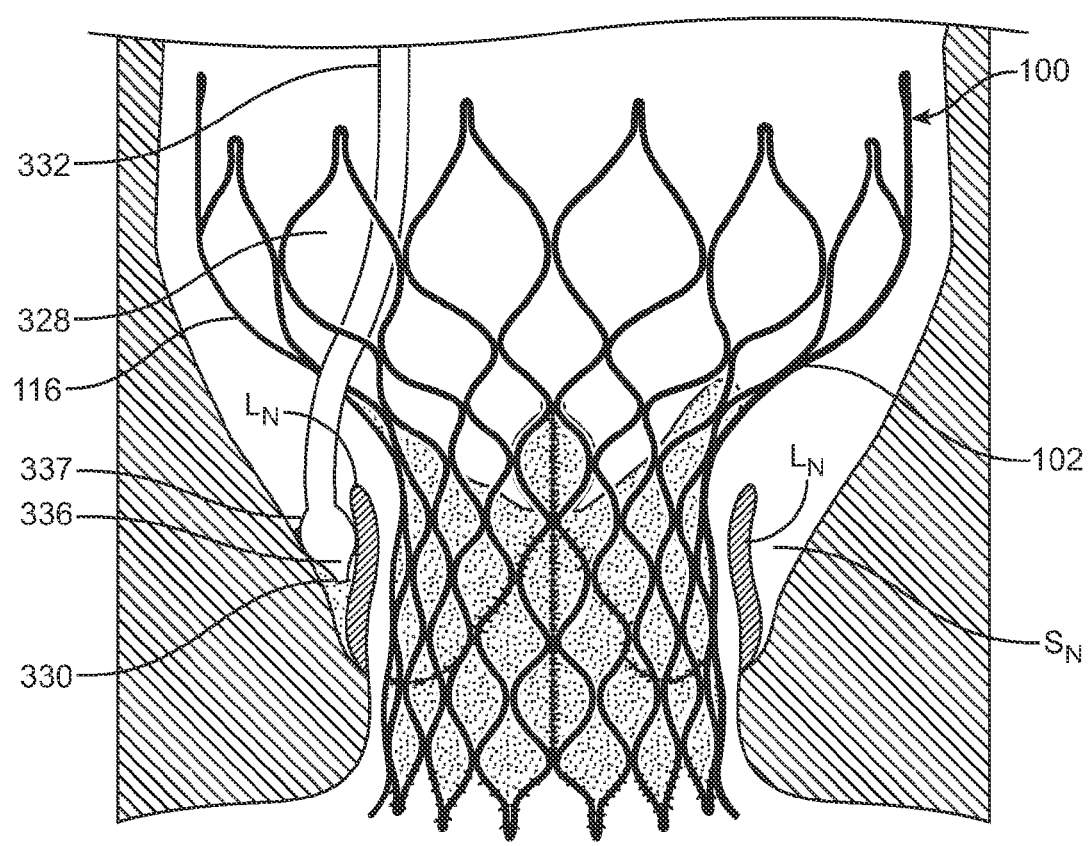
FIG. 3A is a side view illustration of a method of repairing or preventing paravalvular leakage according to an embodiment hereof, wherein an expandable balloon is utilized to direct the injected sealing material into the native valve sinus.

In an embodiment depicted in FIG. 3A, catheter 332 may include an expandable balloon 337 proximal to distal end 336. When expanded in situ within the native valve sinus $S_N$ as shown in FIG. 3A, balloon 337 directs the self-expanding injectable substance in a distal direction upon exiting from distal end 336 of catheter 332 so that sealing element 330 substantially fills native valve sinus $S_N$. Stated another way, balloon 337 operates as an occluding element that blocks or prevents the self-expanding injectable substance from moving in a proximal direction, away from the native valve sinus $S_N$.

In an embodiment depicted in FIG. 4, a blocking catheter may be utilized in a coronary artery during the formation of sealing element 330. More particularly, if sealing element 330 is utilized in the aortic valve, the coronary arteries $C_A$ originate or branch from two of the native valve sinuses. The left coronary artery originates from the left posterior aortic sinus, and the right coronary artery originates from the anterior aortic sinus. Usually, no vessels branch from the right posterior aortic sinus, which is therefore known as the noncoronary sinus. Referring to FIG. 4, a blocking catheter 340 may be placed into at least an ostium of a coronary artery $C_A$ for protection thereof during injection of self-expanding injectable substance 334. In an embodiment, blocking catheter 340 is a balloon catheter having an inflatable balloon 339 at its distal end 338. Blocking catheter 340 is shown after having been introduced into the vasculature via a percutaneous puncture, a.k.a the Seldinger technique, and having been tracked through the vasculature, over the aortic arch and into the descending aorta. Distal end 338 of blocking catheter 340 may be threaded through openings 328 of first section 116 of stent 102, and positioned within the ostium of coronary artery $C_A$. Blood flow is permitted through a lumen (not shown) of blocking catheter 340 to allow for perfusion of coronary artery $C_A$ during the formation of sealing element 330. Balloon 339 is inflated such that its outer surface or diameter is in apposition with a vessel wall of the coronary artery $C_A$ and/or the coronary artery ostium so that self-expanding injectable substance 334 is not permitted or blocked from entering into coronary artery $C_A$. Balloon 339 is shown in its inflated configuration in FIG. 4. Conventional balloon catheters that may be used as blocking catheter 340 include any type of catheter known in the art, including over-the-wire catheters, rapid-exchange catheters, core wire catheters, and any other appropriate balloon catheters. For example, conventional balloon catheters such as those shown or described in U.S. Pat. Nos. 6,736,827; 6,554,795; 6,500,147; and 5,458,639, which are incorporated by reference herein in their entirety, may be modified for use herein.

In an embodiment, the injectable substance that forms a sealing element may expand or solidify upon heating. More particularly, referring to FIG. 5, a delivery catheter 532 is advanced such that a distal end 536 thereof is located adjacent to or within a native valve sinus $S_N$. Catheter 532 includes an electrode 542 adjacent distal end 536, and may be for example a catheter having an electrode at its distal end for radiofrequency (RF) ablation and a lumen for irrigation or delivery of a therapeutic substance, such as that described in U.S. Pat. No. 8,083,732 to Arless et al., assigned to Medtronic Cryocath LP, herein incorporated by reference in its entirety. Although FIG. 5 illustrates a single catheter for delivery and heating of an injectable substance, it would be understood by one of ordinary skill in the art that a first catheter may be used for delivery of injectable substance and a second, separate catheter may be used for heating of the injectable substance. An injectable substance 534 is delivered through catheter 532 and is introduced into a native valve sinus $S_N$. In a first embodiment, expansion of injectable substance 534 is activated via heat from electrode 542 such that upon heating, injectable substance 534 expands within the base of native valve sinus $S_N$ to push native valve leaflet $L_N$ against the outside surface or perimeter of heart valve prosthesis 100, thereby substantially filling any gaps which are present between heart valve prosthesis 100 and the native valve annulus. In a second embodiment, injectable substance 534 is self-expanding upon exiting catheter 532 similar to injectable substance 334 described above with respect to FIG. 3. However, solidification or firming of self-expanding injectable substance 534 is activated via heat from electrode 542 such that upon heating, injectable substance 534 forms a sealing element 530 that remains in situ within native valve sinus $S_N$. Suitable materials for self-expanding injectable substance 534 include but are not limited to a silicone sealant or adhesive.

Figure 6:
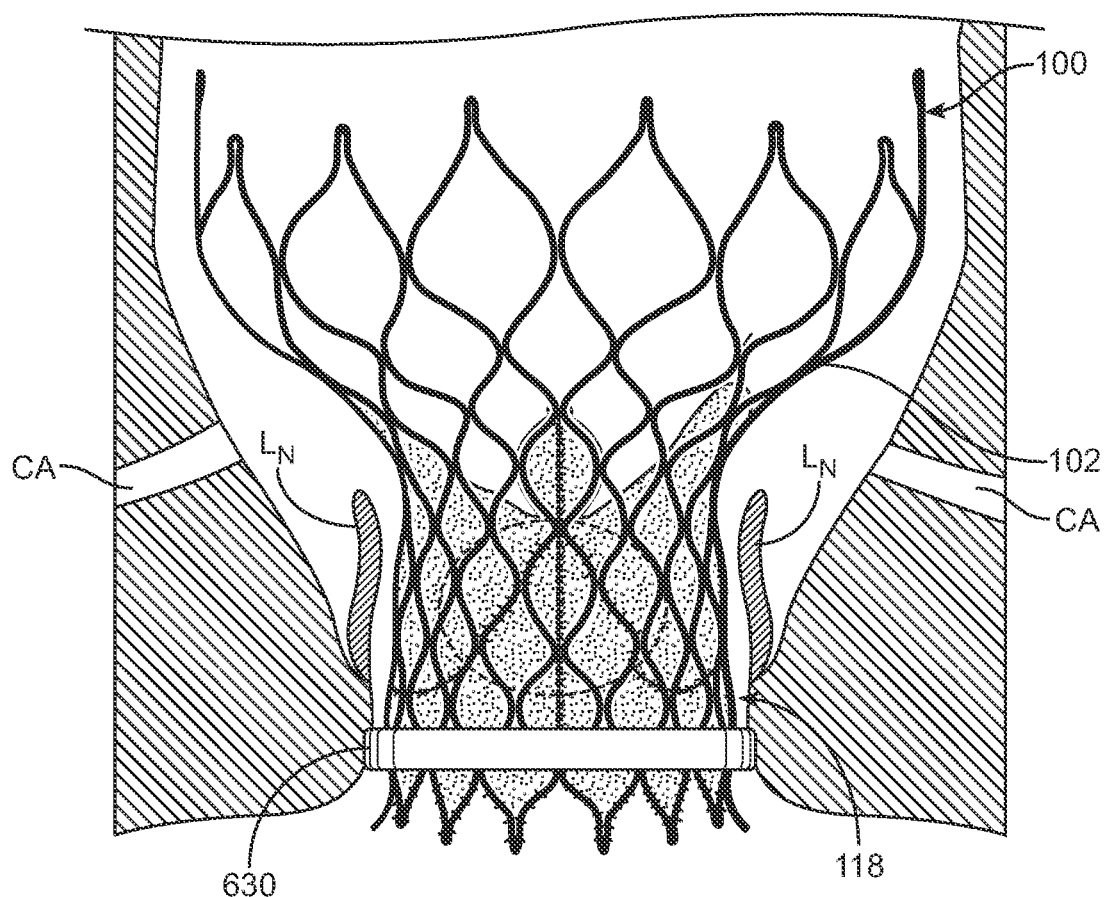
FIG. 6 is a side view illustration of a method of repairing or preventing paravalvular leakage at an aortic valve according to an embodiment hereof, wherein annular sealing material is positioned around an outer surface of a previously implanted heart valve prosthesis.
Figure 7:
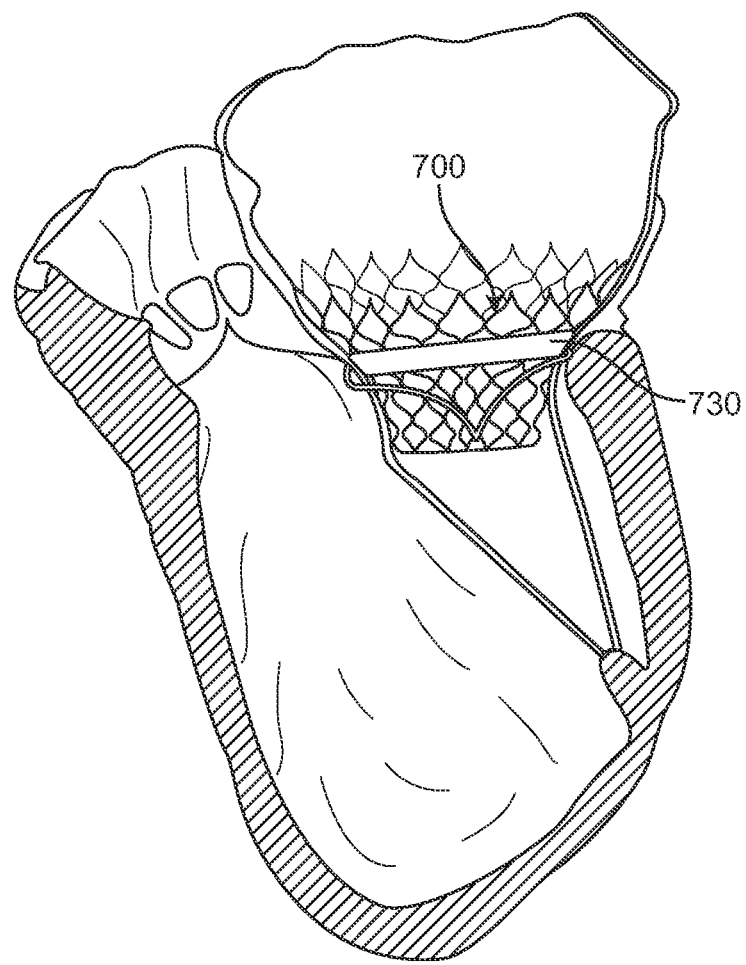
FIG. 7 is a side view illustration of a method of repairing or preventing paravalvular leakage at a mitral valve according to an embodiment hereof, wherein annular sealing material is positioned around an outer surface of a previously implanted heart valve prosthesis.

In other embodiments hereof, an annular sealing element may be placed around the outer surface or perimeter of heart valve prosthesis 100, post-implantation of the heart valve prosthesis, to repair and/or prevent paravalvular leakage. More particularly, FIG. 6 illustrates an annular sealing element 630 around the outer surface or perimeter of heart valve prosthesis 100 implanted within an aortic valve. Annular sealing element 630 may be positioned at the valve annulus, slightly above the valve annulus, slightly below the valve annulus, or some combination thereof. Annular sealing element 630 provides a continuous circumferential seal around heart valve prosthesis 100 to prevent blood flow between the outer surface or perimeter thereof and a native heart valve annulus. Although embodiments depicted herein may be described in relation to a heart valve prosthesis previously implanted within an aortic valve, it would be obvious to one of ordinary skill in the art that such embodiments may be applied to heart valve prosthesis implanted within other heart valves. For example, FIG. 7 illustrates an annular sealing element 730 around the outer surface or perimeter of a heart valve prosthesis 700 implanted within a mitral valve. An annular sealing element may be positioned around the outer surface or perimeter of a previously implanted heart valve prosthesis using one of the following delivery methods described herein with respect to FIGS. 8-10.

Figure 8:
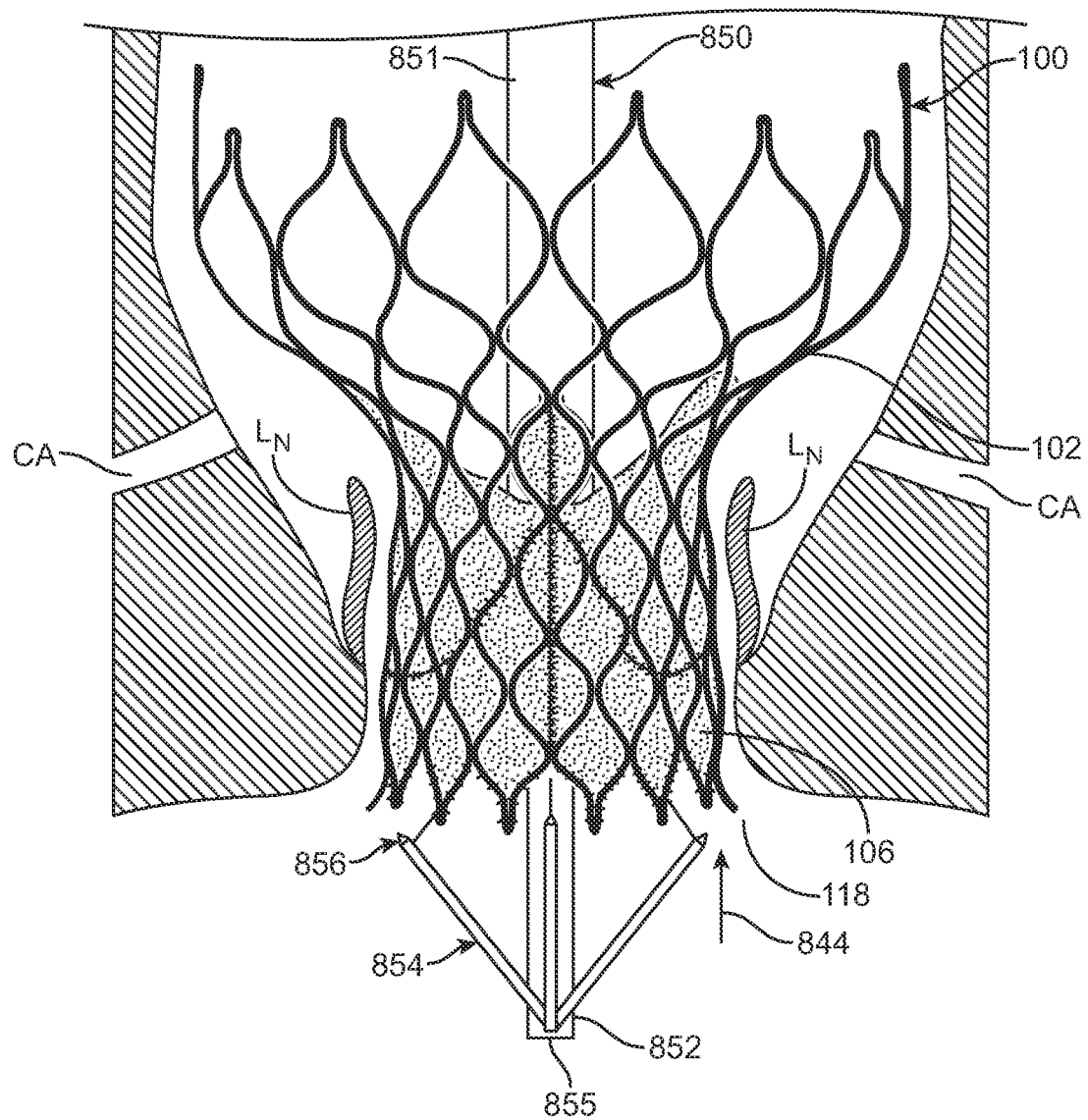
FIGS. 8, 8A, and 8B illustrate a method of and a device for repairing or preventing paravalvular leakage at an aortic valve according to an embodiment hereof, wherein injectable annular sealing material is positioned around an outer surface of a previously implanted heart valve prosthesis via a plurality of needles.
Figure 8A:
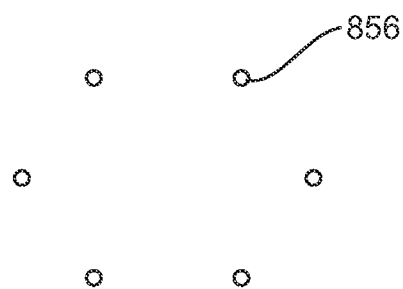
Figure 8B:
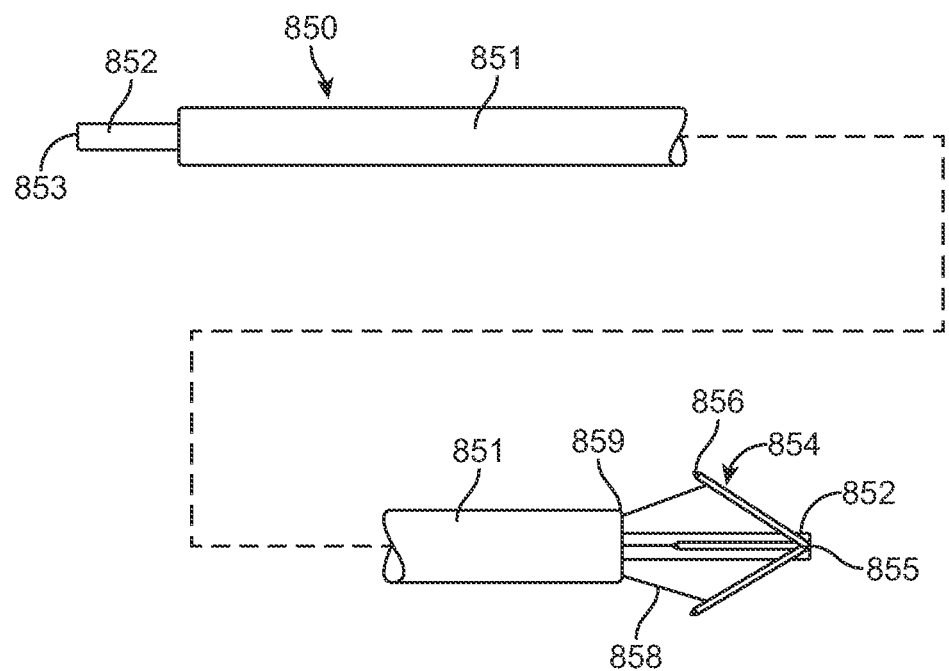

In an embodiment depicted in FIGS. 8, 8A, and 8B, an annular sealing element such as that shown in FIGS. 6 and 7 is formed from an injectable, self-expanding gel or foam that may be delivered via a delivery catheter 850 including a plurality of deployable or radially expandable needles 854. Each needle 854 is a tubular component having a lumen (not shown) there through for delivering the injectable, self-expanding gel or foam. Referring to FIG. 8, delivery catheter 850 is delivered through a previously implanted heart valve prosthesis 100. In an embodiment hereof, placement of the annular sealing element occurs immediately after implantation of heart valve prosthesis 100, and prior to guide wire removal, delivery catheter 850 may be tracked over the same guidewire previously utilized in the delivery of heart valve prosthesis 100. In another embodiment, placement of the annular sealing element occurs during a distinct or secondary procedure from implantation of heart valve prosthesis 100, and thus delivery catheter 850 may be tracked over a new guidewire tracked to the previously implanted heart valve prosthesis. Delivery catheter 850 is advanced in a retrograde manner across previously implanted heart valve prosthesis 100 such that the plurality of needles 854 are located distal to second end 118 of previously implanted heart valve prosthesis 100. After delivery catheter 850 is positioned as desired, the plurality of needles 854 are deployed or radially expanded as shown in FIGS. 8 and 8A, with FIG. 8A depicting an end view of distal tips 856 (with other structure removed for clarity) to illustrate the deployed circular configuration of the plurality of needles 854. Deployment and collapse of needles 854 are discussed in more detail herein with respect to FIG. 8B. When radially expanded, distal tips 856 of the plurality of needles 854 may be spaced apart in approximately equal intervals or segments and form a discontinuous ring or circle, as shown in FIG. 8A. Although shown with six needles 854, it will be understood by one of ordinary skill in the art that a catheter having a greater or lesser number of deployable needles may be utilized herein. Once needles 854 are deployed or radially expanded, delivery catheter 850 is then proximally retracted as shown by directional arrow 844 such that distal tips 856 of the plurality of needles 854 pass through or within second end 118 of heart valve prosthesis 100 and then pierce and pass through graft material 106 of heart valve prosthesis 100 such that distal tips 856 are positioned circumferentially around the outer surface of previously implanted heart valve prosthesis 100. Distal tips 856 may be pointed, sharpened, beveled, or have another configuration suitable for piercing through graft material 106 of heart valve prosthesis 100. With distal tips 856 so positioned, the injectable, self-expanding gel or foam is delivered through inner shaft 852, into needles 854, and out distal tip 856. When the injectable, self-expanding gel or foam exits distal tips 856, the injectable, self-expanding gel or foam spreads away from distal tips 856 and tracks circumferentially around the native valve tissue to merge into an annular sealing element such as that shown in FIG. 6. The number of needles 854 and spacing therebetween may be designed to optimize the formation of the annular sealing element.

Although the annular sealing element of FIG. 6 is shown around second end 118 of heart valve prosthesis 100, catheter 850 may utilize needles 854 to form an annular sealing element anywhere along the length of the heart valve prosthesis. Since the annular sealing element is formed after implantation of heart valve prosthesis 100, longitudinal placement and/or the size and shape thereof is flexible and may be adjusted or adapted according to each application and to a patient's unique needs. For example, depending on the anatomy of the particular patient, the annular sealing element may be formed between heart valve prosthesis 100 and the interior surfaces of the native valve leaflets $L_N$, between heart valve prosthesis 100 and the interior surfaces of the native valve annulus, and/or between heart valve prosthesis 100 and the interior surfaces of the left ventricular outflow track (LVOT).

In another embodiment hereof (not shown), catheter 850 may include a lesser number of deployable needles 854 and the annular sealing element may be formed through a series of injections coupled with rotation of catheter 850. In yet another embodiment hereof (not shown), catheter 850 may include a lesser number of deployable needles 854 that are configured to deliver sealing material at discrete, or non-continuous, locations around the perimeter of a previously implanted heart valve prosthesis. For example, sealing material may be delivered only at the commissures of the native valve.

Once the annular sealing element is formed, delivery catheter 850 may be moved in a distal direction such that distal tips 856 of needles 854 pass back through graft material 106 of heart valve prosthesis. The plurality of needles 854 may then be collapsed, as will be explained in more detail herein, and catheter 850 may be removed from the patient. When needles 854 are withdrawn through the graft material, small delivery holes may be present within graft material 106. Since such delivery holes are located adjacent to the annular sealing member and are of sufficiently small dimension, no leakage occurs there through. In an embodiment, however, additional injectable, self-expanding gel or foam may be delivered through needles 854 to fill and seal these delivery holes prior to further withdrawal of the needles. In another embodiment, graft material 106 is a self-sealing material and such delivery holes close after removal of needles 854.

FIG. 8B illustrates a side view of catheter 850, with needles 854 in a deployed or radially expanded configuration. Catheter 850 includes an outer sheath 851 and an inner shaft 852 extending there through. A proximal end 853 of inner shaft 852 extends out of the patient, and is in fluid communication with a source of the injectable, self-expanding gel or foam. Each needle 854 is connected to and proximally extends from a distal end 855 of inner shaft 852, and the lumen of each needle 854 is in fluid connection with a lumen (not shown) of shaft 852 for delivery of the injectable, self-expanding gel or foam.

In an embodiment hereof, the plurality of needles 854 are formed from a self-expanding material such as NiTi (Nitinol) and deployment and collapse of needles 854 are accomplished via movement of outer sheath 851 relative to inner shaft 852. To deploy needles 854, outer sheath 851 is retracted relative to inner shaft 852 such that a distal end 859 thereof clears or releases distal tip 856 and needles 854 are allowed to self-expand. A plurality of linkages 858 proximally extend from distal tips 856 and proximal ends (not shown) of the linkages remain contained within outer sheath 851. Although not visible in FIG. 8, the proximal ends of the linkages may be coupled to a ring (also not shown) that is slidingly positioned over inner shaft 852. When it is desired to collapse needles 854, outer sheath 851 is distally advanced along linkages 858, thereby collapsing needles 854 such that distal tip 856 fit within distal end 859 of the sheath. The ring that restrains or holds the proximal ends of the linkages ensures that the proximal linkage ends do not flare away from catheter 850 if they unintentionally become uncovered or released from outer sheath 851, while allowing the proximal linkage ends to slide along an outer surface of inner shaft 852 for deployment and collapse.

In another embodiment hereof, rather than forming needles 854 from a self-expanding material, a proximal end of the linkages 858 may be connected to a distal end of a sliding tube or shaft (not shown) that is slidingly disposed over inner shaft 852 and extends to a proximal end of the catheter. The sliding tube or shaft is pushed and/or pulled by the operator to effectuate deployment and collapse of needles 854. To deploy needles 854, outer sheath 851 is retracted to expose needles 854. The sliding tube or shaft may be pushed or distally advanced relative to inner shaft 852 to radially extend linkages 858, thereby radially expanding needles 854 connected thereto by pushing them away from inner shaft 852. When it is desired to collapse needles 854, the sliding tube or shaft may be pulled or proximally retracted relative to inner shaft 852 to radially collapse linkages 858, thereby radially collapsing needles 854 connected thereto by pulling them towards inner shaft 852. Linkages 858 may include a bend or joint (not shown) along their length for effectuating radial extension and collapse thereof. After needles 854 are collapsed, outer sheath 851 is distally advanced relative to inner shaft 852 to cover the needles 854 and delivery catheter 850 may be removed from the patient.

In another embodiment hereof, the annular sealing element is formed via circumferential delivery of an injectable self-expanding substance such as gel or foam around an end of the heart valve prosthesis. More particularly, referring to FIG. 9, a delivery catheter 960 is shown with a conical or frustoconical umbrella-like delivery component 964 in its deployed or expanded configuration for circumferentially delivering an injectable self-expanding substance. Delivery catheter 960 includes an outer shaft 963 which is slidingly disposed over an inner shaft 961, which both extend proximally outside of the patient in situ. Umbrella-like delivery component 964 includes a plurality of circumferentially-spaced apart spokes or support arms 967, the distal ends of which are coupled to a distal end 962 of inner shaft 961 and the proximal ends of which are unattached to be radially extended away from inner shaft 961. Umbrella-like delivery component 964 also includes a plurality of segments 965 extending between adjacent spokes 967. Each segment 965 is formed via a double-layer of fabric or flexible material and defines a lumen or port 966 between the material layers. Each lumen/port 966 is in fluid communication with a central lumen (not shown) of catheter 960, i.e., a lumen defined by inner shaft 963, for delivery of the injectable self-expanding substance. Umbrella-like delivery component 964 is deployed or expanded to the configuration shown in FIG. 9 via a plurality of linkages or hinges 958, the distal ends of which are coupled to a distal end 968 of outer shaft 963. In this configuration, hinges 958 are proximally-extending relative to distal end 968 of outer shaft 963 with the proximal ends thereof are coupled to spokes 967. When outer shaft 963 is pulled or retracted in a proximal direction, the distal ends of hinges 958 also are pulled or retracted in a proximal direction, which causes the proximal ends of hinges 958, coupled to spokes 967, to radially extend away from outer shaft 963 and thereby radially expand spokes 967. Conversely, when it is desired to collapse umbrella-like delivery component 964, outer shaft 963 having the distal ends of hinges 958 coupled thereto is pushed or advanced in a distal direction to cause both hinges 958 and spokes 967 to radially collapse. Thus, outer shaft 963 is pushed and/or pulled by the operator to effectuate extension and collapse of linkages 958, and therefore deployment and collapse of umbrella-like delivery component 964. In another embodiment hereof (not shown), the hinges may be distally extending relative to distal end 968 of outer shaft 963 with the proximal ends thereof coupled to distal end 968 of outer shaft 963 and the distal ends thereof coupled to spokes 967. In the distally extending configuration of the hinges, pushing or distal advancement of outer shaft 963 causes radial expansion of spokes 967 and pulling or proximal retraction of outer shaft 963 causes radial collapse of spokes 967.

Figure 9:
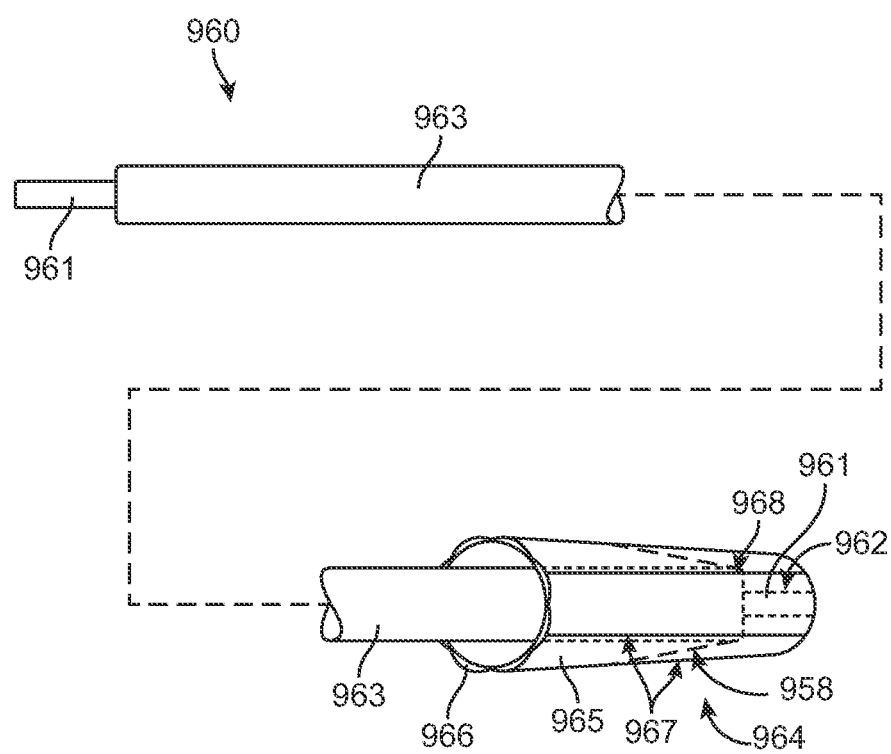
FIGS. 9, 9A-9D illustrate a method of and a device for repairing or preventing paravalvular leakage at an aortic valve according to an embodiment hereof, wherein injectable annular sealing material is positioned around an outer surface of a previously implanted heart valve prosthesis via circumferential delivery of the sealing material.
Figure 9A:
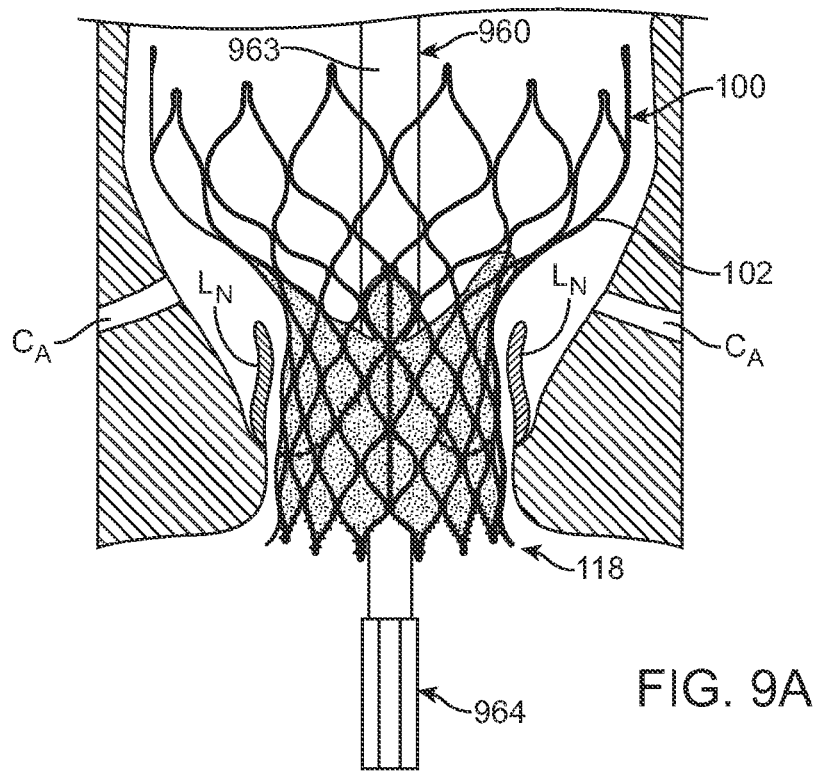

Turning now to FIG. 9A, a method of using delivery catheter 960 to form an annular sealing element around an end of a heart valve prosthesis will be described. As described with respect in previous embodiments, placement of the annular sealing element may occur immediately after implantation of heart valve prosthesis 100 and thus may utilize the same guidewire previously utilized in the delivery of heart valve prosthesis 100, or placement of the annular sealing element may occur during a distinct or secondary procedure from implantation of heart valve prosthesis 100 and thus utilize a new guidewire tracked to the previously implanted heart valve prosthesis. Delivery catheter 960 is advanced in a retrograde manner across previously implanted heart valve prosthesis 100 such that umbrella-like delivery component 964 is located distal to second end 118 of heart valve prosthesis 100 as shown in FIG. 9A. As shown in FIG. 9A, during delivery thereof, umbrella-like delivery component 964 is in a collapsed or non-expanded configuration. Although not shown, an outer sheath may cover the umbrella-like delivery component during delivery thereof.

Figure 9B:
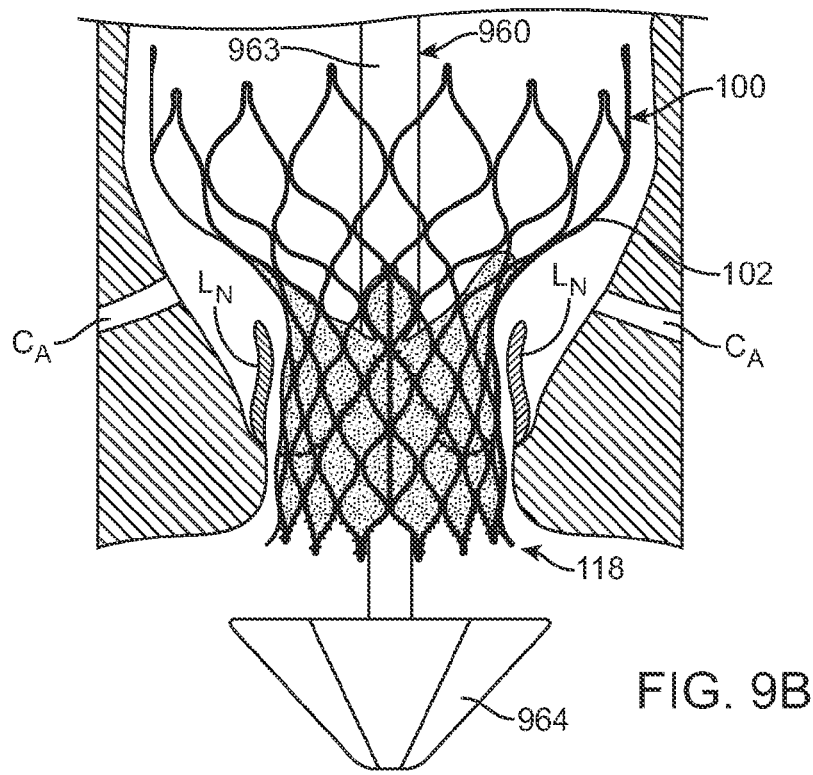

After umbrella-like delivery component 964 is positioned as desired, umbrella-like delivery component 964 is deployed distal to second end 118 of previously implanted heart valve prosthesis 100 as shown in FIG. 9B. Umbrella-like delivery component 964 is deployed via proximal retraction of outer shaft 963 as described above with respect to FIG. 9. In an embodiment hereof, umbrella-like delivery component 964 is deployed solely via extension and collapse of linkages/hinges 958 so that a clinician/operator may control or customize the amount of opening of umbrella-like delivery component 964 to fit the appropriate circumference of previously implanted heart valve prosthesis 100 in the anatomy in which it sits. In another embodiment hereof, umbrella-like delivery component 964 may be formed from a self-expanding material such as stainless steel, a nickel titanium alloy or Nitinol, or a self-expanding polymer, to assist in deployment thereof. The position of outer shaft 963 may be locked in place at a proximal end of catheter 960 in order to temporarily hold or lock hinges/linkages 958 in the extended position, thereby temporarily holding or locking umbrella-like delivery component 964 in the deployed or expanded configuration.

Figure 9C:
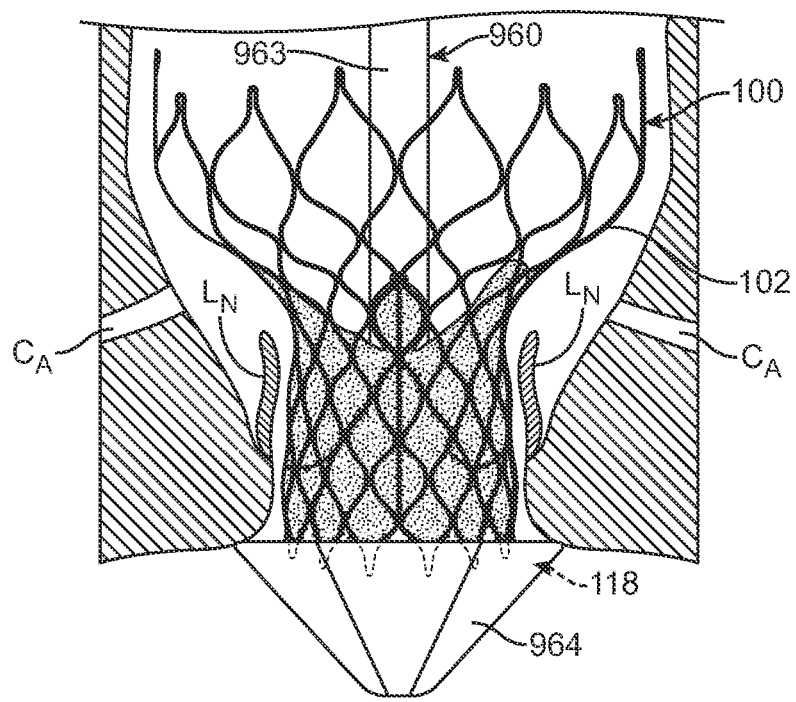
Figure 9D:
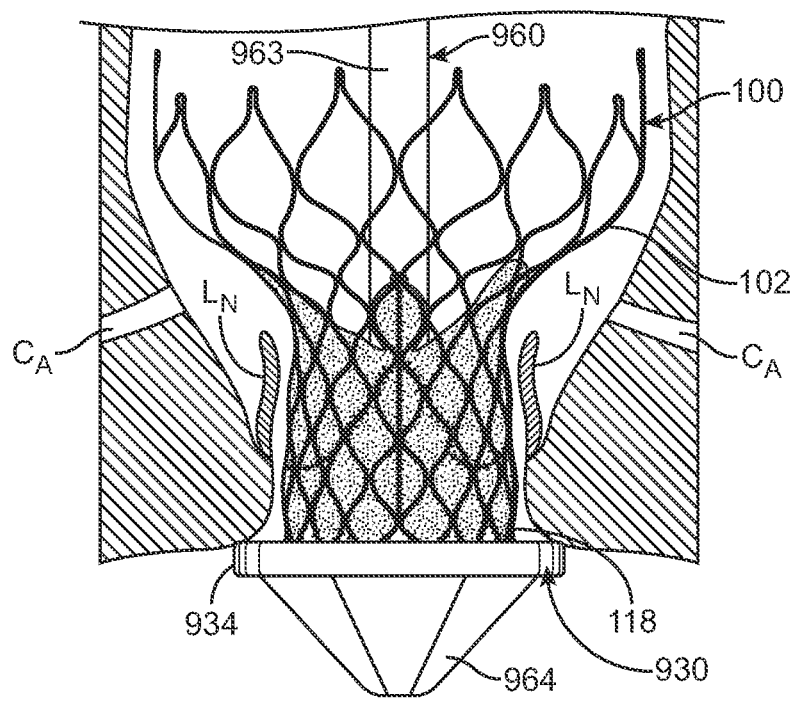

Delivery catheter 960 is then proximally retracted such that umbrella-like delivery component 964 fits over and around second end 118 of previously implanted heart valve prosthesis 100 as shown in FIG. 9C. Umbrella-like delivery component 964 is expanded to a diameter slightly greater than the expanded diameter of second end 118 of previously implanted heart valve prosthesis 100. A self-expanding injectable substance 934 is delivered through a lumen (not shown) of catheter 960 and exits from ports 966 of umbrella-like delivery component 964 as shown in FIG. 9D. The plurality of ports 966 of umbrella-like delivery component 964 circumferentially deliver self-expanding injectable substance 934 around second end 118 of previously implanted heart valve prosthesis 100. Similar to other embodiments hereof, suitable materials for self-expanding injectable substance 934 include but are not limited to hydrogel or a collagen foam/sponge similar to the material commercially available under the trademark Angioseal. Once self-expanding injectable substance 934 exits catheter 960, it self-expands around the outer surface or perimeter of heart valve prosthesis 100 to form an annular sealing element 930 which provides a continuous circumferential seal around heart valve prosthesis 100 to prevent blood flow between the outer surface or perimeter of heart valve prosthesis 100 and the native heart valve. After delivery from catheter 960, self-expanding injectable substance 934 solidifies or firms such that it forms annular sealing element 930 that remains in situ around heart valve prosthesis 100. Once annular sealing element 930 is formed, delivery catheter 960 may be proximally advanced such that umbrella-like delivery component 964 is distal to second end 118 of previously implanted heart valve prosthesis 100. Umbrella-like delivery component 964 is collapsed via distal advancement of outer shaft 963 as described above with respect to FIG. 9, and catheter 960 may be removed from the patient.

Figure 10A:
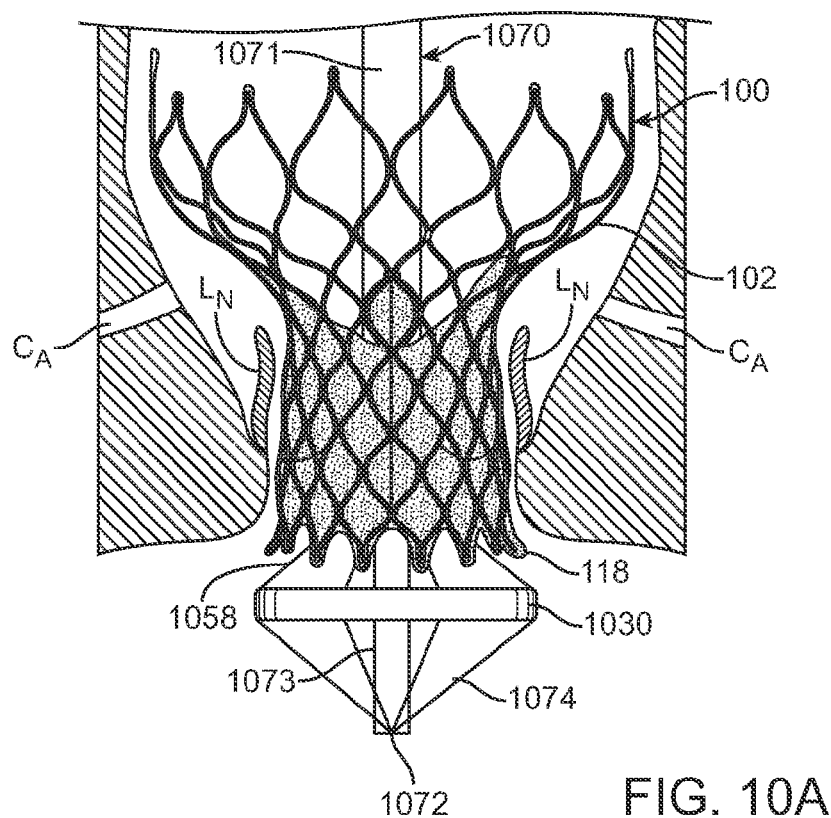
FIGS. 10A-10B illustrate a method of repairing or preventing paravalvular leakage at an aortic valve according to an embodiment hereof, wherein a preformed annular sealing element is positioned around an outer surface of a previously implanted heart valve prosthesis.

In another embodiment hereof, the annular sealing element is a preformed continuous circular band that is percutaneously positioned around a previously implanted heart valve prosthesis. More particularly, referring to FIGS. 10A-10B, a delivery catheter 1070 is delivered through a previously implanted heart valve prosthesis 100. As described with respect to FIG. 8, placement of the annular sealing element may occur immediately after implantation of heart valve prosthesis 100 and thus may utilize the same guidewire previously utilized in the delivery of heart valve prosthesis 100, or placement of the annular sealing element may occur during a distinct or secondary procedure from implantation of heart valve prosthesis 100 and thus utilize a new guidewire tracked to the previously implanted heart valve prosthesis. Delivery catheter 1070 is advanced such that a distal end 1072 thereof is located distal to second end 118 of previously implanted heart valve prosthesis 100. After delivery catheter 1070 is positioned as desired, a plurality of support arms 1074 radially expand an annular sealing element or component 1030 as shown in FIG. 10A. Distal ends of support arms 1074 are coupled to an inner shaft 1073, while annular sealing element or component 1030 encircles proximal ends of support arms 1074. In an embodiment hereof, to deploy support arms 1074, the support arms are formed from a self-expanding material such as NiTi (Nitinol) and deployment and collapse thereof is accomplished via retraction of an outer sheath 1071 and a plurality of linkages 1058 having proximal ends still contained within the outer sheath to operate similar to the linkages described with respect to FIG. 8B. In another embodiment hereof, to deploy support arms 1074, proximal ends of linkages 1058 are connected to a distal end of a sliding tube or shaft (not shown) that is slidingly disposed over inner shaft 963 and extends to a proximal end of the catheter. The sliding tube or shaft may be pushed and/or pulled by the operator to effectuate deployment and collapse of support arms 1074.

Figure 10B:
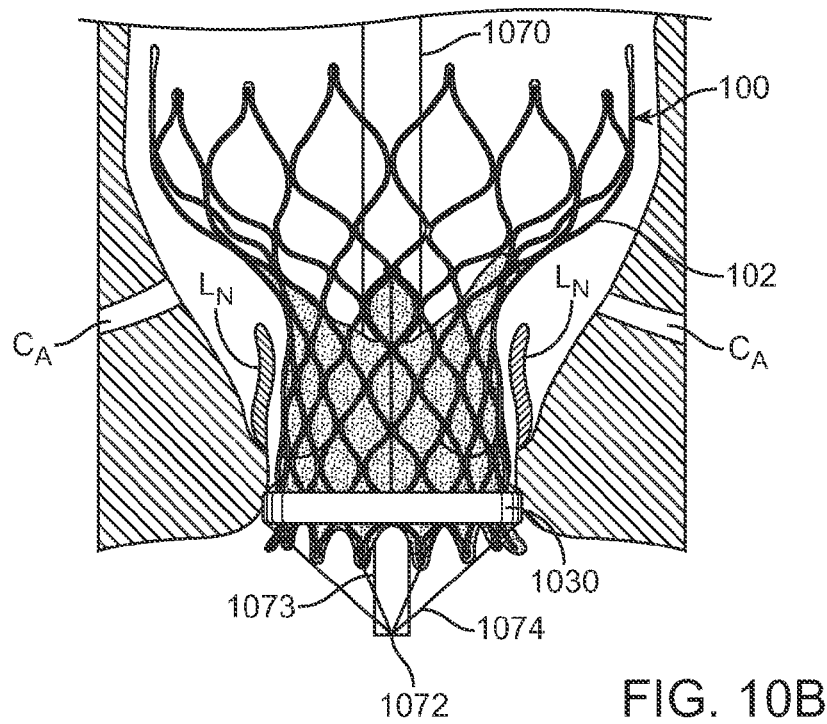

Delivery catheter 1060 is then proximally retracted such that annular sealing element or component 1030 fits over and around second end 118 of previously implanted heart valve prosthesis 100 as shown in FIG. 10B. Annular sealing element or component 1030 has an expanded outer diameter greater than the expanded diameter of second end 118 of previously implanted heart valve prosthesis 100 such that it functions to substantially seal any/all gaps between the heart valve prosthesis and the native valve tissue. In an embodiment hereof, annular sealing element or component 1030 is formed from an elastic material and may be stretched over second end 118 of previously implanted heart valve prosthesis 100 without recapture and/or collapse of stent 102. In another embodiment hereof, as described in more detail herein with respect to FIGS. 14A-14E, a portion the previously implanted heart valve prosthesis may be recaptured and collapsed to assist in positioning annular sealing element 1030 over second end 118 of the heart valve prosthesis. Once annular sealing element 1030 is in place as desired, delivery catheter 1070 may be proximally advanced such that the plurality of support arms 1074 are distal to second end 118 of previously implanted heart valve prosthesis 100. Linkages 1058 are radially collapsed, such as via advancement of outer sheath 1071 or by pulling the sliding tube or shaft, in order to collapse the plurality of support arms 1074. Catheter 1060 may be removed from the patient.

In an embodiment hereof, annular sealing element 1030 may be formed from a swellable material that collapses easily and expands to a larger volume after implantation, such as but not limited to hydrogel or a collagen foam/sponge similar to the material commercially available under the trademark Angioseal. After annular sealing element 1030 is positioned around second end 118 of heart valve prosthesis 100, the material of annular sealing element 1030 expands/swells into contact with native tissue such that it engages and conforms to the inner surface of the valve annulus including any surface irregularities that may be present. As such, annular sealing element 1030 provides a continuous circumferential seal around heart valve prosthesis 100 to prevent blood flow between the outer surface or perimeter of heart valve prosthesis 100 and the native heart valve. The composition of the swellable material may be configured to tailor the absorption rate thereof such that annular sealing element 1030 does not radially expand until it is positioned around second end 118 of heart valve prosthesis 100.

In another embodiment hereof, annular sealing element 1030 may be formed from an elastic material that provides a continuous circumferential seal around heart valve prosthesis 100 to prevent blood flow between the outer surface or perimeter of heart valve prosthesis 100 and the native heart valve. "Elastic" as used in this context includes materials that may be stretched or elongated to fit over and around second end 118 of heart valve prosthesis 100, while also having sufficient resiliency to resume their original size/configuration and conform to the outer surface of the heart valve prosthesis. Suitable polymer materials include polymer materials such as polyurethane or silicone, as well as biological or natural materials such as pericardium or another membranous tissue such as intestinal submucosa. The elastic annular sealing element 1030 has sufficient resiliency to hold conform to and be secured over the outer surface of the heart valve prosthesis, but does not exert an amount of force that would result in constriction or reduction of the inner diameter of the heart valve prosthesis.

In yet another embodiment hereof, annular sealing element 1030 may be a hollow sac or membrane that is configured to be filled with an inflation medium that is delivered through a lumen (not shown) of catheter 1070 and the plurality of support arms 1074. In this embodiment, the plurality of support arms 1074 need be in fluid communication with the lumen of the hollow sac or membrane of annular sealing element 1030 via one or more inflation ports (not shown). Suitable materials for the membrane include flexible/pliable polymers such as ePTFE, polyurethane, or silicone and suitable inflation medium include but are not limited to gels, biocompatible polymers including curable polymers, gases, saline, blood, and the like. As the inflation medium is delivered, annular sealing element 1030 radially expands into contact with native tissue such that it engages and conforms to the inner surface of the valve annulus including any surface irregularities that may be present. The annular sealing element 1030 is inflated to such an extent that a sufficient or satisfactory seal is created between prosthesis 100 and the inner surface of the native valve annulus. The expanded annular sealing element 1030 is compliant and fills any/all gaps existing between the prosthesis and the native valve tissue but does not reduce the inner diameter of prosthesis 100. The inflation ports of annular sealing element 1030 may be sealed off to maintain constant pressure within the annular sealing element. In an embodiment, injectable, self-expanding gel or foam may be delivered to fill the inflation ports. In another embodiment, the material of the hollow sac or membrane is a self-sealing material and the inflation ports close after removal of support arms 1074. In yet another embodiment, the inflation ports may include one-way check valves that allow passage of the inflation medium and prevent leakage/removal of the inflation medium after delivery thereof.

Figure 11A:
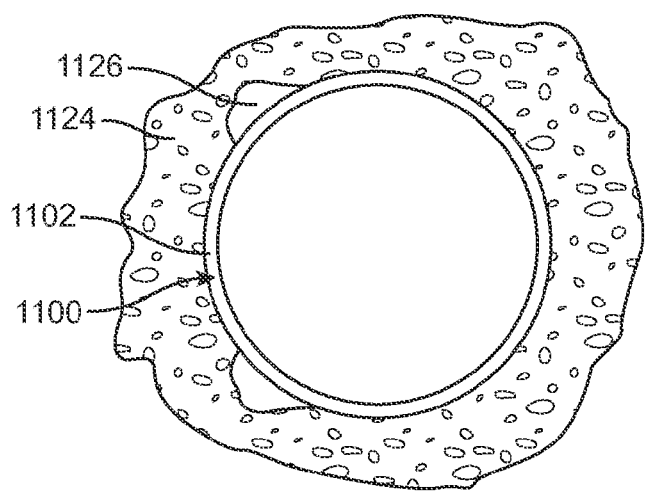
FIGS. 11A-11B illustrate a method of repairing or preventing paravalvular leakage at a heart valve according to an embodiment hereof, wherein a preformed annular sealing element is positioned within a previously implanted heart valve prosthesis to press a support frame or stent of the previously implanted heart valve prosthesis against native valve tissue.
Figure 11B:
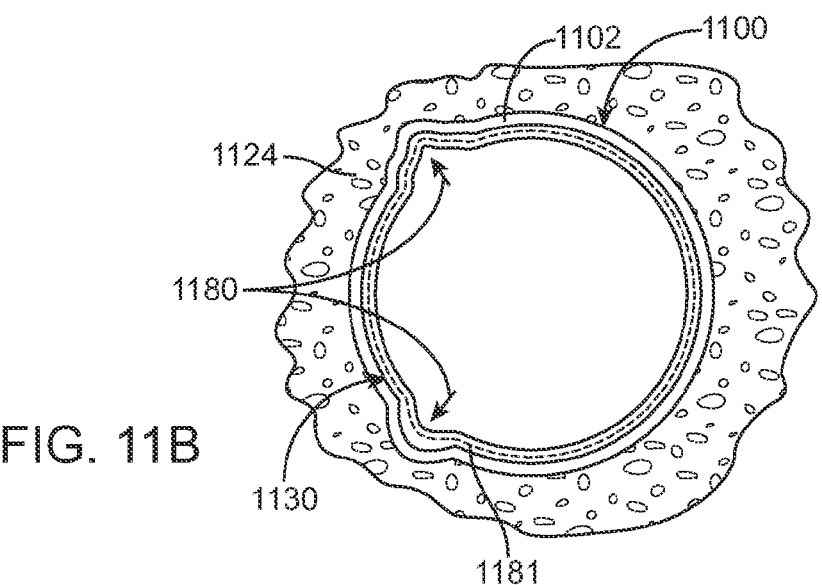
Figure 12:
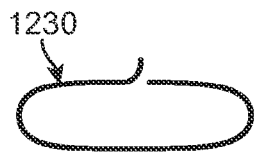
FIG. 12 is a perspective view of an alternative preformed annular sealing element having a single loop or winding that may be positioned within a previously implanted heart valve prosthesis to press a support frame or stent of the previously implanted heart valve prosthesis against native valve tissue.

In other embodiments hereof shown in FIGS. 11A, 11B and 12, an annular sealing element may alternatively and/or additionally be placed within a heart valve prosthesis 100, post-implantation of the heart valve prosthesis, to repair and/or prevent paravalvular leakage. More particularly, referring to the cross-sectional view of FIG. 11A, a heart valve prosthesis 1100 having a support frame or stent 1102 is shown deployed within a native valve annulus 1124. Gaps or cavities 1126 are present between an outer surface of stent 1102 and the native tissue. As shown in FIG. 11B, an annular sealing element 1130 expands against an inner surface of previously implanted heart valve prosthesis 1100 to press stent 1102 against native valve tissue, thereby substantially filling any gaps or cavities 1126. Annular sealing element or component 1130 exerts a radial pressure onto the previously implanted heart valve prosthesis 1100 in a radially outward direction represented by the directional arrow 1180. More particularly, an expanded or deployed outer diameter of annular sealing element or component 1130 is predetermined to be slightly greater than the expanded outer diameter of stent 1102. When deployed, annular sealing element 1130 over-expands stent 1102 until the stent and/or the sealing element fill any/all gaps or cavities between the outer surface of the stent and native valve tissue. Due to annular sealing element 1130 having an expanded diameter slightly greater than the expanded diameter of stent 1102 of previously implanted heart valve prosthesis 1100, annular sealing element 1130 is secured within heart valve prosthesis 110 via a friction or interference fit after deployment.

Annular sealing element 1130 may be delivered and radially expanded with a delivery catheter such as delivery catheter 1070 having a plurality of support arms 1074 described in relation to FIGS. 10A and 10B. In an embodiment hereof, annular sealing element 1130 may be formed from a flexible/pliable polymer material such as polyurethane or silicone. Annular sealing element 1130 may include a braided wire or element 1181 therein to strengthen annular sealing element 1130 and assist in securing annular sealing element 1130 within heart valve prosthesis 110 via a friction or interference fit after deployment. In another embodiment hereof, annular sealing element 1130 may be a hollow sac or membrane that is configured to be filled with an inflation medium that is delivered through a lumen (not shown) of the delivery catheter (not shown) and the plurality of support arms (not shown), as described herein. Suitable materials for the membrane include flexible/pliable polymers such as ePTFE, polyurethane, or silicone and suitable inflation medium include but are not limited to gels, biocompatible polymers including curable polymers, gases, saline, blood, and the like. As the inflation medium is delivered, annular sealing element 1130 radially expands into contact with the previously implanted valve prosthesis and further over-expands or pushes the valve prosthesis such that it conforms to the inner surface of the valve annulus including any surface irregularities that may be present, thereby filling any gaps or cavities that may be present between the valve prosthesis and native tissue. Once the annular sealing element 1130 has been sufficiently inflated such that a satisfactory seal has been created between prosthesis 100 and the inner surface of the valve annulus, any inflation ports of annular sealing element 1130 may be sealed off to maintain constant pressure within the annular sealing element as described in more detail herein with respect to FIGS. 10A-10B.

Figure 13:
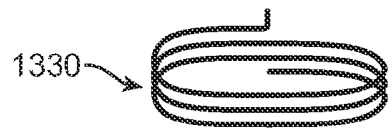
FIG. 13 is a perspective view of an alternative preformed annular sealing element having a plurality of loops or windings that may be positioned within a previously implanted heart valve prosthesis to press a support frame or stent of the previously implanted heart valve prosthesis against native valve tissue.

In another embodiment hereof, the annular sealing element or component deployed within a heart valve prosthesis, post-implantation of the heart valve prosthesis, may be a loop or coil formed from a shape memory material. Annular sealing element 1230 is shown in its deployed configuration in FIG. 12. Annular sealing element 1230 is formed of a shape memory material that is pre-formed or pre-shaped into a deployed configuration, which has a specific geometry such as a single circumferential loop shown in FIG. 12, which in situ is formed in a plane transverse to the longitudinal axis of a previously implanted heart valve (not shown). Annular sealing element 1230 may be substantially straightened or stretched for delivery to the treatment site and returns to its original, preset expanded or deployed shape upon release from the delivery system. In order to self-expand, annular sealing element 1230 may be made from a metallic material having a mechanical memory to return to the preset expanded or deployed shape. Mechanical memory may be imparted to annular sealing element 1230 by thermal treatment to achieve a spring temper in stainless steel, for example, or to set a shape memory in a susceptible metal alloy, such as Nitinol. In an alternate embodiment, a mechanical memory to return to the preset expanded or deployed shape may be imparted to a polymer that forms annular sealing element 1230, such as any of the polymers disclosed in U.S. Pat. Appl. Pub. No. 2004/0111111 to Lin, which is herein incorporated by reference in its entirety. In an embodiment, annular sealing element 1230 is a NiTi (nitinol) wire having a diameter between approximately 0.1 mm to 1.5 mm. The wire forming annular sealing element 1230 may be slightly larger, i.e., have a greater diameter, than a wire forming the heart valve prosthesis in order to have sufficient radial force to over-expand the stent of the heart valve prosthesis. The nitinol wire may have a round or circular cross-section. In other embodiments, the nitinol wire may have an elliptical cross-section, a strip or ribbon-like form or any other suitable cross-sectional configuration. Although annular sealing element 1230 is shown with a single complete winding or loop, it will be apparent to those of ordinary skill in the art that annular sealing element 1230 may have multiple adjacent windings in either a stacked or spaced-apart spring-like form. For example, FIG. 13 illustrates an annular sealing element or component 1330 having a spiral or helical deployed configuration that defines a blood flow lumen through the open center of the helix.

To deliver annular sealing elements 1230, 1330, the annular sealing element or component is substantially straightened into a delivery configuration and distally advanced out of a port of a catheter or sheath. The substantially straightened annular sealing element may be distally advanced through the port of the catheter via a pusher rod or tube that extends within the catheter for the full length thereof, with the proximal end thereof extending outside of the patient. As the substantially straightened annular sealing element or component passes out of the port, it coils or loops against the interior surface of a previously implanted heart valve prosthesis until the proximal end of the annular sealing element exits the catheter.

In another embodiments hereof, an annular sealing element may be placed around the outer surface or perimeter of a heart valve prosthesis, post-implantation of the heart valve prosthesis, to repair and/or prevent paravalvular leakage utilizing an in situ crimper device to radially contract one end of the implanted heart valve prosthesis and thus provide or allow access to the outer surface of the heart valve prosthesis. Referring to FIGS. 14A-14G, a method of using an in situ crimper device 1482 to deliver an annular sealing element 1430 is illustrated. Crimper device 1482 includes a plurality of self-expandable grasper arms 1486 that are coupled to a distal end of an inner shaft or rod (not shown) that is slidingly disposed within an outer shaft 1483. The inner shaft or rod extends to a proximal end of the crimper device, and may be pushed and/or pulled to expand and/or collapse the grasper arms, as described in more detail herein. The plurality of grasper arms 1486 are formed from a self-expanding material such as NiTi (Nitinol), and outer sheath 1483 radially constrains grasper arms 1486 during delivery.

Figure 14A:
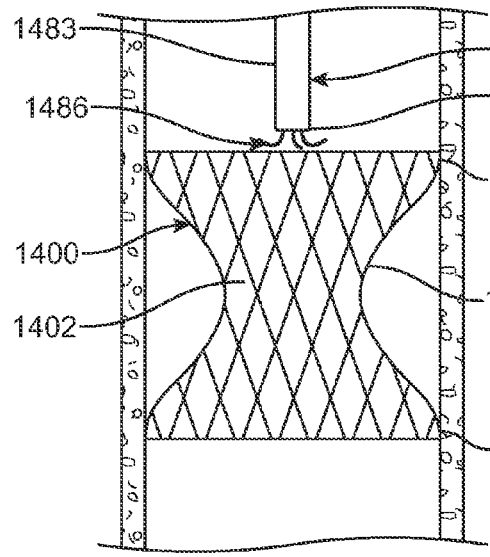
FIGS. 14A-14G illustrate a method of using an in situ crimper device to deliver an annular sealing element.

In FIG. 14A, crimper device 1482 is advanced such that a distal end 1484 of outer sheath 1483 is adjacent to a first or proximal flared end 1416 of a previously implanted heart valve prosthesis 1400. Heart valve prosthesis 1400 has an hourglass configuration in which a stent or support frame 1402 thereof has the proximal flared end 1416, a middle waisted or narrow portion 1417, and a second or distal flared end 1418. As described with respect to previous embodiments hereof, placement of the annular sealing element may occur immediately after implantation of heart valve prosthesis 1400 and thus may utilize the same guidewire previously utilized in the delivery of heart valve prosthesis 1400, or placement of the annular sealing element may occur during a distinct or secondary procedure from implantation of heart valve prosthesis 1400 and thus utilize a new guidewire tracked to the previously implanted heart valve prosthesis.

Figure 14B:
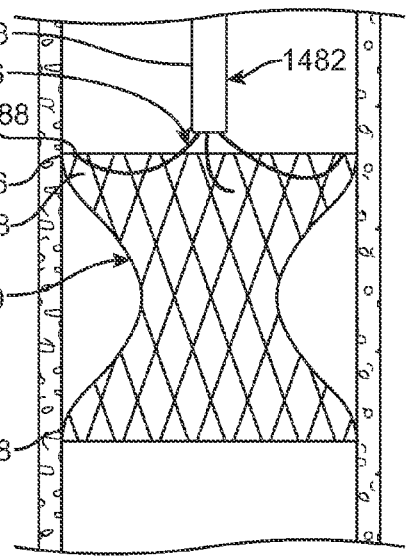

After in situ crimper device 1482 is positioned as desired, the plurality of self-expandable grasper arms 1486 are deployed or radially expanded as shown in FIG. 14B. Although shown with three grasper arms 1486, it will be understood by those of ordinary skill in the art that a greater or less number of deployable grasper arms may be utilized herein. Grasper arms 1486 are deployed via relative motion between the inner shaft or rod and outer sheath 1483. For example, grasper arms 1486 may be distally advanced from distal end 1484 of outer sheath 1483 by pushing inner shaft or rod, thereby exposing grasper arms 1486 and allowing them to self-expand. In another example, grasper arms 1486 may be deployed via retraction of outer sheath 1483, thereby exposing grasper arms 1486 and allowing them to self-expand. When deployed, distal tips 1488 of grasper arms 1486 form curves or hooks that engage or attach to stent 1402, adjacent to proximal flared end 1416. More particularly, distal tips 1488 travel or pass from the inner surface of previously implanted heart valve prosthesis 1400, through openings 1428 formed within stent 1402, and hook around or engage stent 1402.

Figure 14C:
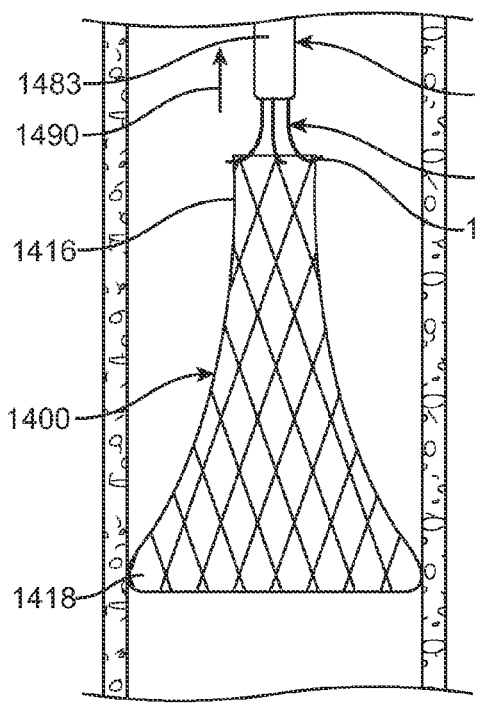

Once grasper arms 1486 are deployed or radially expanded and distal tips 1488 thereof are positioned so as to grasp or engage the previously implanted heart valve prosthesis 1400, grasper arms 1486 are then proximally retracted, illustrated via directional arrow 1490 in FIG. 14C, by pulling the inner shaft or rod. Distal flared end 1418 of previously implanted heart valve prosthesis 1400 remains securely in apposition with the vessel wall, while grasper arms 1486 essentially radially collapse proximal end 1416 of stent 1402 out of apposition with the vessel wall and into a reduced diameter, so that heart valve prosthesis 1400 is in a temporary partially crimped state. In other words, proximal end 1416 of previously implanted heart valve prosthesis 1400 is radially contracted by crimper device 1482 to provide or allow access to the outer surface of the heart valve prosthesis.

In one embodiment hereof (not shown), with proximal end 1416 of previously implanted heart valve prosthesis 1400 radially contracted, an annular sealing element may be formed in situ at any location along the length of heart valve prosthesis 1400, including distal end 1418, via a secondary catheter such as catheter 332 described herein which is configured to deliver an injectable, self-expanding material. The secondary catheter may be delivered alongside in situ crimper device 1482 and tracked or directed around heart valve prosthesis 1400 in order to deliver the sealing material around the outer surface or perimeter of the heart valve prosthesis.

Figure 14D:
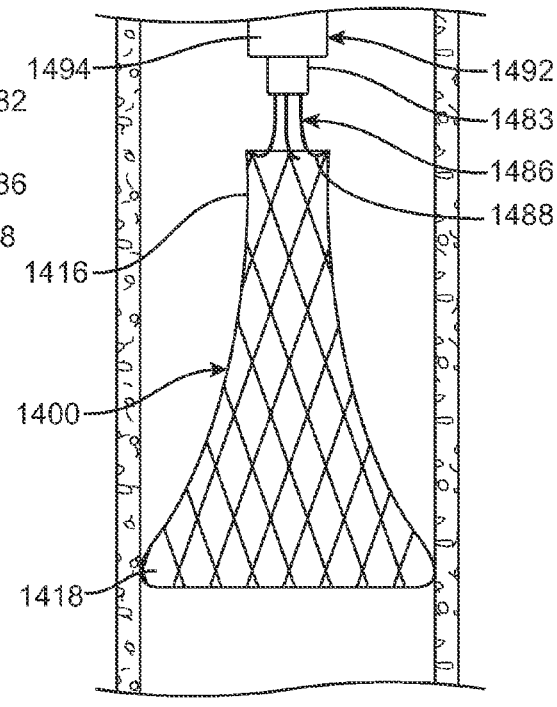
Figure 14E:
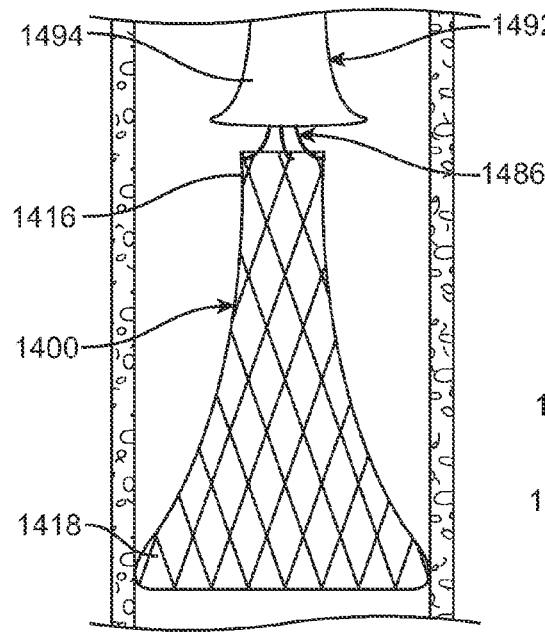

In another embodiment hereof, with proximal end 1416 of previously implanted heart valve prosthesis 1400 radially contracted, an annular sealing element 1430 may be positioned around second or distal end 1418 of the heart valve prosthesis. A delivery catheter 1492 having an expandable distal end portion 1494 is delivered over in situ crimper device 1482 as shown in FIG. 14D. Once distal end 1492 is positioned adjacent to heart valve prosthesis 1400, which is still held in a temporary partially crimped state by grasper arms 1486, distal end 1494 of delivery catheter 1492 is expanded as shown in FIG. 14E. Distal end 1494 is formed from a self-expanding material and expansion and collapse thereof may be accomplished via retraction of an outer sheath (not shown).

Figure 14F:
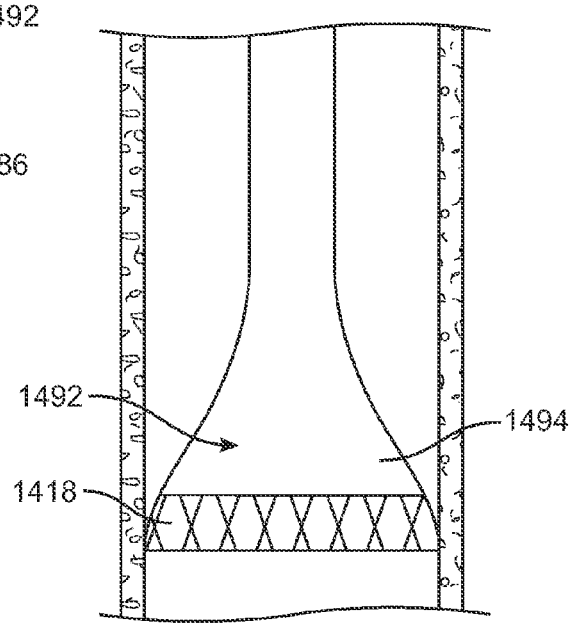

After distal end 1494 is expanded, delivery catheter 1492 is distally advanced over the heart valve prosthesis 1400 as shown in 14F. In one embodiment, expanded distal end 1494 is delivered over the length of heart valve prosthesis 1400 until it is positioned adjacent to distal end 1418 of the heart valve prosthesis as shown in FIG. 14F but it will be understood by one or ordinary skill in the art that the distal end may be positioned anywhere along the length of the heart valve prosthesis, depending upon the desired location of annular sealing element 1430. Although annular sealing element 1430 is shown around second end 1418 of heart valve prosthesis 1400 in FIG. 14G, the annular sealing element may be positioned anywhere along the length of the heart valve prosthesis. Since the annular sealing element is positioned after implantation of heart valve prosthesis 1400, longitudinal placement and/or the size and shape thereof is flexible and may be adjusted or adapted according to each application and to a patient's unique needs.

Figure 14G:
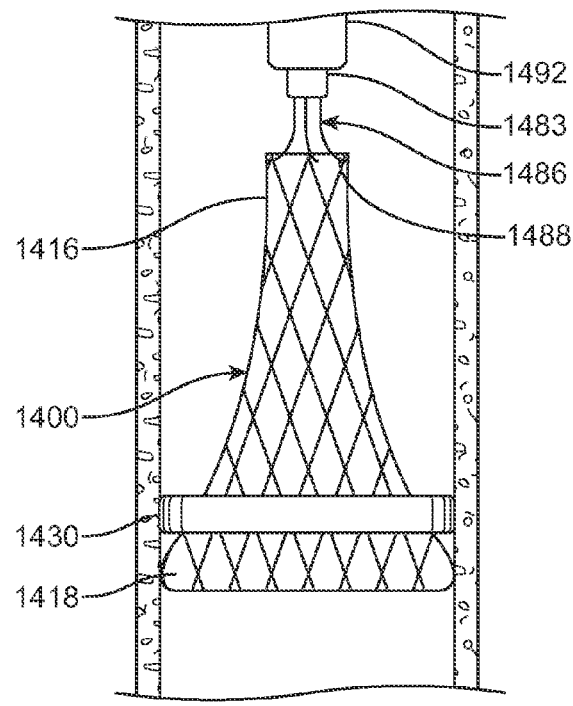

Once distal end 1494 of delivery catheter 1492 is in place, annular sealing element 1430 is formed around or delivered to second or distal end 1418 of heart valve prosthesis 1400 as shown in FIG. 14G. More particularly, in one embodiment, annular sealing element 1430 may be circumferentially formed around heart valve prosthesis from an injectable, self-expanding gel or foam that is delivered via a plurality of lumens and corresponding ports (not shown) formed within distal end 1494 of delivery catheter 1492. In another embodiment, annular sealing element 1430 is a preformed continuous circular band mounted over distal end 1494 of delivery catheter 1492 during delivery thereof which is pushed or distally advanced from distal end 1494 of delivery catheter 1492 onto second or distal end 1418 of heart valve prosthesis via a pusher sheath (not shown) which is slidingly positioned over delivery catheter 1492. In this embodiment, annular sealing element 1430 may be formed from a swellable material that collapses easily and fills to a larger volume after implantation or an elastic conformable material such as polyurethane, silicone, or a biological or natural materials such as pericardium or another membranous tissue such as intestinal submucosa.

Once annular sealing element 1430 is positioned as desired, delivery catheter 1492 is proximally retracted such that distal end 1494 is no longer positioned over heart valve prosthesis 1400 and distal end 1494 thereof may be collapsed for removal as shown in FIG. 14G. Distal end 1494 may be collapsed via distal advancement of an outer sheath (not shown). Delivery catheter 1492 may then be removed from the patient. Grasper arms 1486 may be distally advanced by pushing the inner shaft or rod to disengage distal tips 1488 from stent 1402. Outer sheath 1483 is then advanced over grasper arms 1486 for collapse thereof, and crimper device 1482 may be removed from the patient.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of preventing and/or repairing paravalvular leakage, the method comprising the steps of:
   advancing a catheter to a previously implanted valve prosthesis, wherein the catheter is configured to deliver an injectable sealing material;
   injecting the sealing material around an outer surface of the implanted valve prosthesis via the catheter by extending a plurality of needles of the catheter through graft material of the implanted valve prosthesis and delivering the sealing material through the plurality of needles; and
   allowing the sealing material to expand and solidify in situ to form an annular sealing element that extends between the outer surface of the implanted valve prosthesis and native valve tissue to close and/or prevent gaps between the implanted valve prosthesis and native valve tissue to repair and/or prevent paravalvular leakage.

2. The method of claim 1, further comprising the step of withdrawing the plurality of needles through the graft material, thereby leaving a plurality of small holes in the graft material.

3. The method of claim 2, further comprising the step of injecting additional sealing material into the plurality of holes.

4. A method of preventing and/or repairing paravalvular leakage, the method comprising the steps of:
   advancing a catheter to a previously implanted valve prosthesis, wherein the catheter is configured to deliver an injectable sealing material;
   injecting the sealing material around an outer surface of the implanted valve prosthesis via the catheter by positioning an umbrella-like delivery component of the catheter around an end of the implanted valve prosthesis and delivering the sealing material through the umbrella-like delivery component; and
   allowing the sealing material to expand and solidify in situ to form an annular sealing element that extends between the outer surface of the implanted valve prosthesis and native valve tissue to close and/or prevent gaps between the implanted valve prosthesis and native valve tissue to repair and/or prevent paravalvular leakage.

5. A method of preventing and/or repairing paravalvular leakage, the method comprising the steps of:
   advancing a catheter to a previously implanted valve prosthesis, wherein the catheter is configured to deliver an injectable sealing material;
   injecting the sealing material around an outer surface of the implanted valve prosthesis via the catheter;
   temporarily crimping a first end of the implanted valve prosthesis prior to the step of injecting the sealing material around an outer surface of the implanted valve prosthesis via the catheter; and
   allowing the sealing material to expand and solidify in situ to form an annular sealing element that extends between the outer surface of the implanted valve prosthesis and native valve tissue to close and/or prevent gaps between the implanted valve prosthesis and native valve tissue to repair and/or prevent paravalvular leakage.

6. A method of preventing and/or repairing paravalvular leakage, the method comprising the steps of:
   advancing a catheter to a previously implanted valve prosthesis, wherein the catheter includes an annular sealing component mounted thereon; and
   positioning the annular sealing component onto the implanted valve prosthesis, wherein the annular sealing component is positioned within the implanted valve prosthesis to over-expand and press at least a portion of the implanted valve prosthesis against native valve tissue and wherein the annular sealing component closes and/or prevents gaps between the implanted valve prosthesis and native valve tissue to repair and/or prevent paravalvular leakage.

7. The method of claim 6, wherein the annular sealing component is a hollow polymeric sac and further comprising the step of delivering an inflation medium to the hollow polymeric sac to expand the sac in situ.

8. The method of claim 6, wherein the annular sealing component is a conformable polymeric ring.

9. The method of claim 6, wherein the annular sealing component is at least one loop of a self-expanding shape memory material.

10. The method of claim 1, wherein the plurality of needles of the catheter are spaced apart in equal intervals around the outer surface of the implanted valve prosthesis during the step of injecting the sealing material around the outer surface of the implanted valve prosthesis.

11. The method of claim 1, wherein the plurality of needles each include distal tips configured for piercing through the graft material of the implanted valve prosthesis.

12. The method of claim 1, wherein the step of allowing the sealing material to expand and solidify in situ to form an annular sealing element includes allowing the sealing material to spread away from the plurality of needles and track circumferentially around the implanted valve prosthesis to merge into the annular sealing element.

13. The method of claim 2, wherein the graft material is self-sealing and the plurality of holes self-seal after the plurality of needles are withdrawn.

14. The method of claim 4, wherein the umbrella-like delivery component of the catheter includes a plurality of circumferentially spaced apart support arms and a plurality of segments extending between the adjacent pairs of the support arms, each segment including a double layer of flexible material that defines a port for delivery of the sealing material.

15. The method of claim 14, wherein each support arm includes a hinge for radial expansion and radial collapse thereof.

16. The method of claim 5, wherein the step of injecting the sealing material around the outer surface of the implanted valve prosthesis includes tracking the catheter around the outer surface of the implanted valve prosthesis.

17. The method of claim 5, wherein the step of injecting the sealing material around the outer surface of the implanted valve prosthesis includes circumferentially delivering the sealing material through a plurality of lumens and corresponding ports formed within a distal end of the catheter.

18. The method of claim 6, wherein the annular sealing component has an expanded outer diameter that is predetermined to be greater than an expanded diameter of the implanted valve prosthesis.

19. The method of claim 7, further comprising the step of sealing of an inflation port of the hollow polymeric sac after delivery of the inflation medium.

20. The method of claim 9, wherein the annular sealing component has a substantially straightened delivery configuration during the step of advancing the catheter and wherein the annular sealing component self-expands against an interior surface of the implanted valve prosthesis during the step of positioning the annular sealing component onto the implanted valve prosthesis.

* * * * *